US008680014B2

(12) United States Patent
Zhang et al.

(10) Patent No.: US 8,680,014 B2
(45) Date of Patent: Mar. 25, 2014

(54) METHODS FOR IMPROVING FRUIT PRODUCTION AND FRUIT QUALITY

(75) Inventors: Caixi Zhang, Shanghai (CN); Matthew D. Whiting, Prosser, WA (US)

(73) Assignee: Washington State University Research Foundation, Pullman, WA (US)

( * ) Notice: Subject to any disclaimer, the term of this patent is extended or adjusted under 35 U.S.C. 154(b) by 75 days.

(21) Appl. No.: 13/107,658

(22) Filed: May 13, 2011

(65) Prior Publication Data

US 2011/0281730 A1 Nov. 17, 2011

Related U.S. Application Data

(60) Provisional application No. 61/334,419, filed on May 13, 2010, provisional application No. 61/334,434, filed on May 13, 2010, provisional application No. 61/352,531, filed on Jun. 8, 2010.

(51) Int. Cl.
*A01N 37/00* (2006.01)

(52) U.S. Cl.
USPC .................................. 504/320; 252/70; 47/2

(58) Field of Classification Search
USPC .................................. 504/320; 47/2; 252/70
See application file for complete search history.

(56) References Cited

U.S. PATENT DOCUMENTS

| 6,495,572 | B1 * | 12/2002 | Cohen | 514/339 |
| 6,534,446 | B1 * | 3/2003 | Kinnersley et al. | 504/147 |
| 2007/0113304 | A1 * | 5/2007 | Demmer et al. | 800/289 |

OTHER PUBLICATIONS

"A novel product for frost protection in sweet cherry," Washington State University Cherry Field Day, 2009 (1 page).
"APOGEE® Plant Growth Regulator," BASF Corporation, 2008 (11 pages).
Cline et al., "Performance of prohexadione-calcium on shoot growth and fruit quality of apple—Effect of spray surfactants," *Canadian Journal of Plant Science*, vol. 88, pp. 165-174, 2008.
Hansen, "Understanding cherry fruit set," http://www.goodfruit.com/Good-Fruit-Grower/March-15th-2011/Understanding-cherry-fruit-set/, 2011 (3 pages).
Pak and Kim, "Effect of 4-Chlorophenoxyacetic Acid on Fruit Set and Nutrient Accumulation in *Cucurbita moschata* (Duch.) Poir," ISHS Acta Horticulturae 483: International Symposium on Vegetable Quality of Fresh and Fermented Vegetables, 1997, Abstract (1 page).
"PGRs to improve fruit quality," Washington State University Cherry Field Day, 2009 (1 page).
Slaughter et al., "Beta-aminobutyric acid-induced resistance in grapevine against downy mildew: involvement of pterostilbene," *Eur. J. Plant Pathol.*, vol. 122, pp. 185-195, 2008.
Whiting et al., "Efficient production of superlative fruit," http://jenny.tfrec.wsu.edu/wtfrc/PDFfinalReports/2010FinalReports/Whiting_final.pdf, 2010 (11 pages).
Zhang and Whiting, Manipulating sweet cherry fruit set with plant growth regulators, International Society for Horticultural Science, 6$^{th}$ International Cherry Symposium, 2009, Abstract (1 page).
Zhang and Whiting, "Improving 'Bing' sweet cherry fruit quality with plant growth regulators," *Scientia Horticulturae*, vol. 127, pp. 341-346, 2011.
Zhang and Whiting, "Pre-harvest foliar application of Prohexadione-Ca and gibberellins modify canopy source-sink relations and improve quality and shelf-life of 'Bing' sweet cherry," *Plant Growth Regul.*, DOI: 10.1007/s10725-011-9584-z, 2011 (12 pages).

* cited by examiner

*Primary Examiner* — Rebecca Prouty
*Assistant Examiner* — Danielle Sullivan
(74) *Attorney, Agent, or Firm* — Whitham, Curtis, Christofferson & Cook, P.C.

(57) ABSTRACT

Disclosed herein are methods for improving fruit production or fruit quality in fruit trees, such as decreasing cold damage, increasing fruit size, increasing fruit quality, and/or increasing fruit set. In some embodiments, the disclosed methods include methods of decreasing cold damage to a fruit tree including applying an effective amount of a composition including DL-β-aminobutyric acid to the fruit tree, thereby decreasing cold damage, for example as compared to a control. In other embodiments, the disclosed methods include methods of increasing fruit size or fruit quality of fruit from a fruit tree, including applying an effective amount of a composition including prohexadione-calcium to the fruit tree after anthesis, thereby increasing fruit size or fruit quality, for example as compared to a control. In further embodiments, the disclosed methods include methods of increasing fruit size of fruit from a fruit tree or increasing fruit set of a fruit tree including applying an effective amount of a composition including 4-chlorophenoxyacetic acid to the fruit tree, thereby increasing fruit size or fruit set, for example as compared to a control.

7 Claims, 18 Drawing Sheets

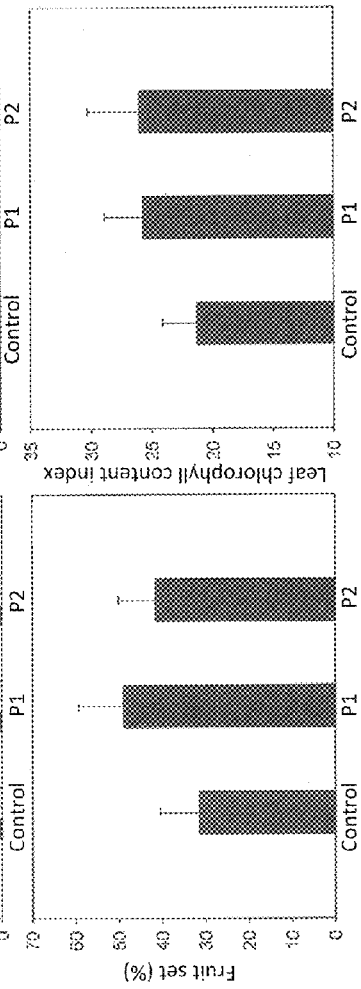
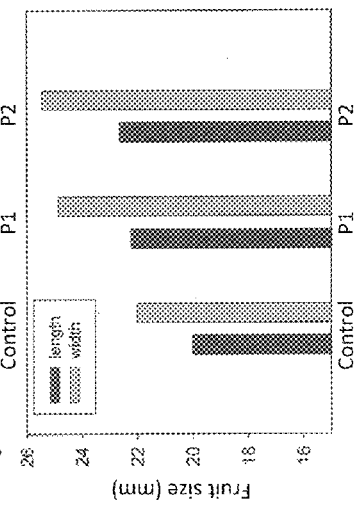
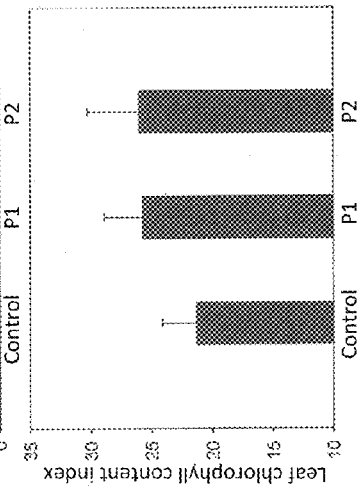
FIG. 1A
FIG. 1B
FIG. 1C
FIG. 1D
FIG. 1E

US 8,680,014 B2

METHODS FOR IMPROVING FRUIT PRODUCTION AND FRUIT QUALITY

CROSS REFERENCE TO RELATED APPLICATIONS

This claims the benefit of U.S. Provisional Application No. 61/334,419, filed May 13, 2010, U.S. Provisional Application No. 61/334,434, filed May 13, 2010, and U.S. Provisional Application No. 61/352,531, filed Jun. 8, 2010, each of which is incorporated herein by reference in their entirety.

ACKNOWLEDGMENT OF GOVERNMENT SUPPORT

This invention was made with government support under award number 2010-31100-06053 awarded by the United States Department of Agriculture. The government has certain rights in the invention.

FIELD

This disclosure relates to methods for improving aspects of fruit production and fruit quality of fruit trees, particularly utilizing plant growth regulators or a non-peptide amino acid.

BACKGROUND

There has been a recent worldwide increase in cherry production, with 2009 crop production reaching two million metric tons (*World Sweet Cherry Review*, Belrose, Inc., Pullman, Wash., 2009). Factors such as fluctuating winter temperatures, spring frosts, rain-induced fruit cracking, and bird losses make cherry production challenging. Similar challenges are present in other fruit crops, including plum, peach, nectarine, apple, and pear crops. Thus, there is a need for methods to improve fruit production and fruit quality.

SUMMARY

Disclosed herein are methods for improving fruit production and/or fruit quality in fruit trees, such as decreasing cold damage, increasing fruit size, increasing fruit quality, and/or increasing fruit set.

In some embodiments, the disclosed methods include methods of decreasing cold damage to a fruit tree including applying an effective amount of a composition including DL-β-aminobutyric acid (BABA) to the fruit tree, thereby decreasing cold damage, for example as compared to a control.

In other embodiments, the disclosed methods include methods of increasing fruit size or fruit quality of fruit from a fruit tree, including applying an effective amount of a composition including prohexadione-calcium (PCa) to the fruit tree after anthesis, thereby increasing fruit size or fruit quality, for example as compared to a control. In some embodiments, the disclosed methods include applying an effective amount of a composition including PCa and one or more gibberellins (such as gibberellin A3 ($GA_3$), gibberellin A4 ($GA_4$), gibberellin A7 ($GA_7$), or a combination of two or more thereof) to the fruit tree after anthesis. In particular examples, the composition (such as a composition including PCa or a composition including PCa and one or more GA) is applied to the tree at about 20 to 45 days after anthesis.

In further embodiments, the disclosed methods include methods of increasing fruit size of fruit from a fruit tree or increasing fruit set of a fruit tree including applying an effective amount of a composition including 4-chlorophenoxyacetic acid (CPA) to the fruit tree, thereby increasing fruit size or fruit set, for example as compared to a control. In some examples, the composition is applied to the fruit tree during flowering or post-bloom.

In some examples of the disclosed methods, the composition is applied to leaves, buds, flowers, or branches of the tree, or a combination of two or more thereof, for example by spraying. In some examples, the fruit tree is a stone fruit tree, such as a sweet cherry, tart cherry, plum, peach, nectarine, or apricot tree. In other examples, the fruit tree is a pome fruit tree, such as an apple, pear, quince, or loquat tree.

The foregoing and other features of the disclosure will become more apparent from the following detailed description, which proceeds with reference to the accompanying figures.

BRIEF DESCRIPTION OF THE DRAWINGS

FIG. 1A-E is a series of graphs showing the effect of BABA on sweet cherry cv. 'Bing' at −3.5° C. and −4.5° C. FIG. 1A, flower fate (% flowers killed); FIG. 1B, fruit set; FIG. 1C, fruit size; FIG. 1D, average leaf area; FIG. 1E, leaf chlorophyll content index. Control, untreated; P1, BABA, 100 ppm; P2, BABA, 500 ppm.

DETAILED DESCRIPTION

I. Abbreviations

Figure 2:
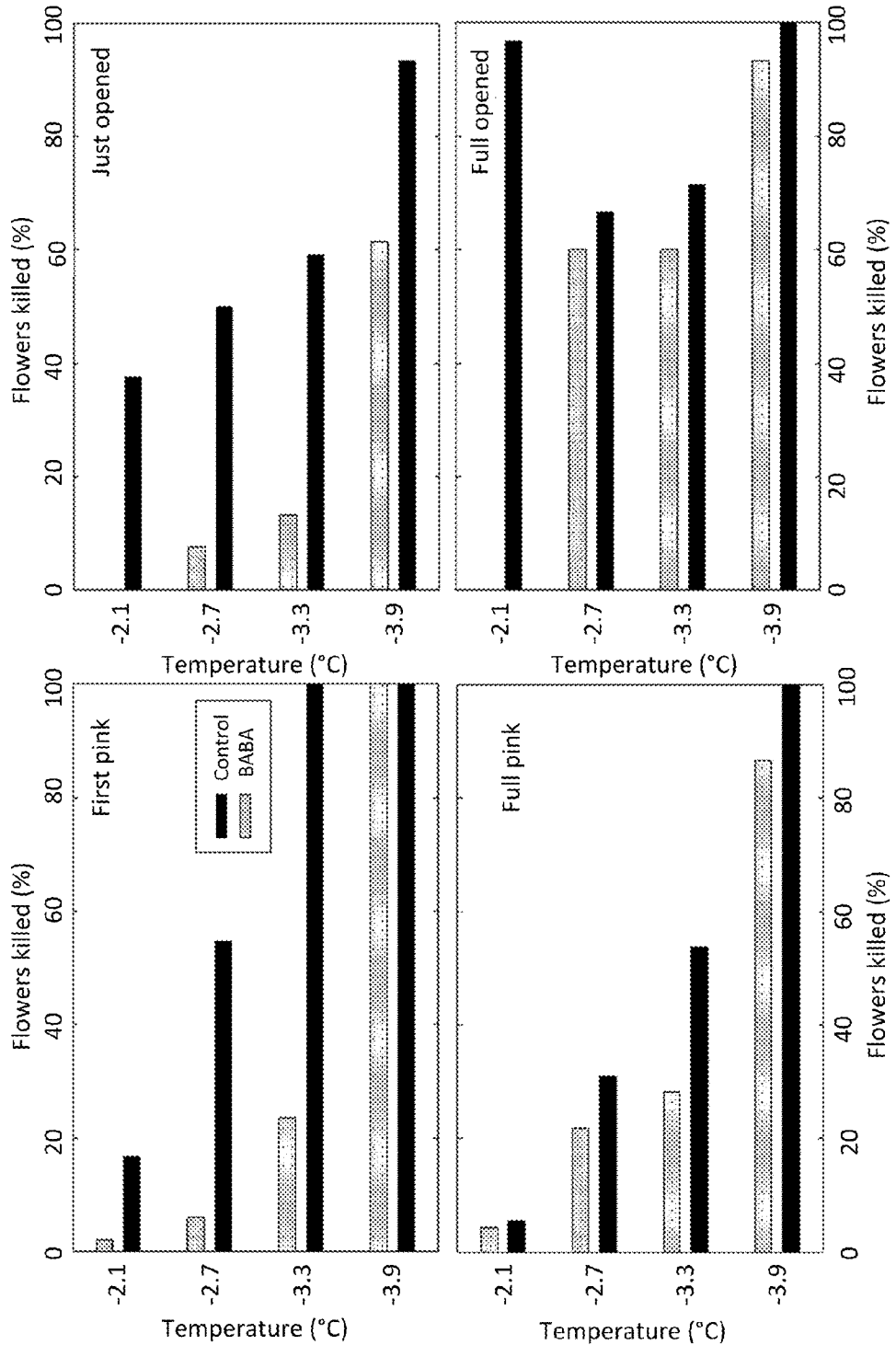
FIG. 2 is a series of panels showing flower hardiness of 'Fuji' apple at the indicated flower bud developmental stages and temperatures in BABA-treated and untreated (control) branches. Branches were treated with BABA 5 days prior to cold temperature exposure.

| | |
|---|---|
| BABA: | DL-β-aminobutyric acid |
| CPA (4-CPA): | 4-chlorophenoxyacetic acid |
| GA: | gibberellin |
| PCa | prohexadione-calcium |
| ppm | parts per million |

II. Terms

Unless otherwise noted, technical terms are used according to conventional usage. Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Although methods and materials similar or equivalent to those described herein can be used in the practice or testing of the present disclosure, suitable methods and materials are described below.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

DL-β-aminobutyric Acid (BABA):

Also known as DL-3-aminobutyric acid. A compound having the following structure:

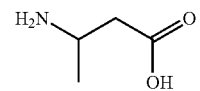

BABA is a non-protein amino acid known to induce resistance to biotic and abiotic stresses in plants (e.g., Jakab et al., *Eur. J. Plant Pathol.* 107:29-37, 2001; Cohen, *Plant Dis.* 86:448-457, 2002).

Anthesis:

The time of flowering of a plant, for example, the opening of a flower bud. In some examples, anthesis is the time that a flower is accessible to a pollinator (such as a bee).

Applying (to a Tree):

Contacting a tree or a portion of a tree (such as leaves, buds, flowers, branches, trunk, roots, or a combination of two or more thereof) with an agent or composition.

4-chlorophenoxyacetic Acid (CPA):

Also known as parachlorophenoxyacetate or 4-chlorophenoxyacetate. A compound having the structure:

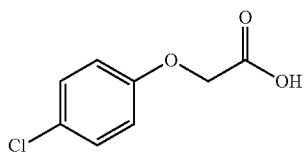 [SMILES: O=C(O)COc1ccc(Cl)cc1]

CPA is an auxin that is used in agriculture as an herbicide.

Control:

A "control" refers to a sample or standard used for comparison with an experimental sample. In some embodiments, a control is an untreated fruit tree or portion of a fruit tree (such as one or more branches, buds, flowers, leaves, or a combination thereof). A control (such as an "untreated" control) may be a fruit tree or portion thereof to which no composition or treatment has been applied, or may be a fruit tree or portion thereof to which an inert compound or carrier has been applied (such as water). In other examples, a control is a fruit tree or portion thereof which has been treated with a different composition for the sake of comparison. In some embodiments, the control is a historical control or standard reference value or range of values (such as a previously tested control sample, such as a group of untreated trees that represent baseline or normal values, such as fruit size, fruit quality, fruit set, or cold damage).

Effective Amount:

An amount or dose sufficient to achieve a desired effect, such as decreasing cold damage, increasing fruit size, increasing fruit quality, and/or increasing fruit set of a fruit tree, for example as compared to a control.

Fruit Set:

An event where a flower's ovary is fertilized and will grow into fruit. The term fruit set includes the proportion or percentage of flowers which develop into a fruit. In some examples, fruit set includes initial fruit set (proportion of flowers that form fruitlets) and/or final fruit set (proportion of flowers that become mature fruit and/or remain until commercial harvest). Fruit set is assessed by counting flowers in a limb or tree during anthesis (available flowers) and later counting viable fruitlets or fruit from the same limb or tree.

Fruit Tree:

A tree bearing edible fruit, such as fruit for human consumption. In some examples, a fruit tree is a stone fruit tree. A stone fruit (or drupe) is a fruit with a fleshy outer part surrounding a one or a few seeds enclosed in a stony layer derived from the ovary wall of the flower. Exemplary stone fruit include sweet cherry (e.g., *Prunus avium*), tart (or sour) cherry (e.g., *Prunus cerasus*), plum (e.g., *Prunus domestica*, *Prunus salicina*, or *Prunus insititia*), peach (e.g., *Prunus persica*), nectarine (e.g., *Prunus persica* var. *nucipersica*), and apricot (e.g., *Prunus armeniaca*). In other examples, a fruit tree is a pome fruit tree. A pome is a fruit in which the seeds are protected by a tough carpel wall and the entire fruit is embedded in a fleshy receptacle. Exemplary pomes include apple (e.g., *Malus domestica*), pear (e.g., *Pyrus communis* or *Pyrus pyrifolia*), quince (e.g., *Cydonia oblonga*), and loquat (e.g., *Eriobotrya japonica*).

Gibberellin (GA):

A family of more than one hundred tetracyclicditerpenes that regulate plant growth and development. Bioactive GAs are involved in several aspects of plant development, such as seed germination, flower induction and fruit and seed development. In some examples, GAs are tetracyclicditerpenoid carboxylic acids having a 20-nor-ent-gibberellene skeleton, a carboxyl group on C-6, a lactone function between C-4 and C-10, and a hydroxyl or other functionality at C-3β. In some examples, gibberellins include gibberellin A1 (GA1), gibberellin A3 (GA3), gibberellin A4 (GA4), gibberellin A7 (GA7), or a combination of two or more thereof. For example, GA4/7 indicates a mixture of GA4 and GA7. The structures of GA3, GA4 and GA7 are shown below.

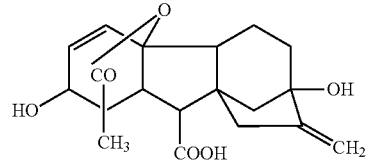

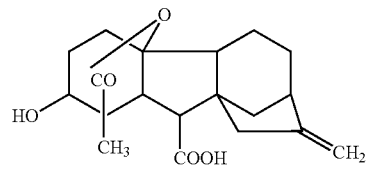

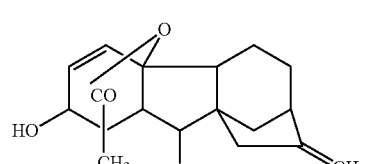

Prohexadione-Calcium (PCa):

Also known as calcium 3-oxido-4-propionyl-5-oxo-cyclohexene carboxylate. A compound having the structure:

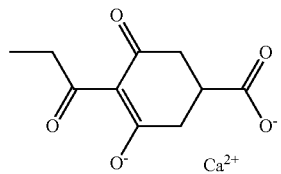

PCa is an inhibitor of GA biosynthesis.

III. Methods of Decreasing Cold Damage

Disclosed herein are methods of decreasing cold damage to a fruit tree. The methods include applying to the fruit tree (or a portion thereof) an effective amount of a composition including DL-β-aminobutyric acid (BABA), thereby decreasing cold damage to the fruit tree as compared to a control. In some examples, the methods decrease cold damage to a fruit tree that occurs when temperatures (such as air temperatures) are about 5° C. or less (such as, but not limited to about 5° C., 4° C., 3° C., 2° C., 1° C., 0° C., −1° C., −2° C., −3° C., −4° C., −5° C., −6° C., −7° C., −8° C., −9° C., −10° C., −11° C., −12° C., −13° C., −14° C., −15° C., −16° C., −17° C., −18° C., −19° C., −20° C., −25° C., −30° C., or less). In other examples, the methods decrease damage to a fruit tree at temperatures of about 5° C. to −40° C. (for example, about −5° C. to −30° C., −10° C. to −20° C., 4° C. to −10° C., or 0° C. to −5° C.). In some examples, the disclosed methods decrease cold damage to a fruit tree when the tree is exposed to cold temperatures (for example, about 0° C. or less) for at least about 10 minutes (such as, but not limited to at least about 30 minutes or about 1, 2, 3, 4, 6, 8, 10, 12, 16, 18, 20, 24, 36, 48, or more hours). One of skill in the art can identify temperatures and lengths of exposure that are likely to cause cold damage based on the type of fruit tree, developmental stage of buds, flowers, or fruit, overall tree health, tree vigor, tree nutritional status, and so on.

In some embodiments, the methods include applying the composition to fruit tree leaves, buds, flowers, branches, or a combination of two or more thereof. In particular examples, the composition is applied to the tree by spraying, for example spraying with a solution including BABA. In some examples, the composition is applied (for example sprayed) on the fruit tree or portion thereof until it runs off the tree (for example, the leaves, buds, flowers, and/or branches). In other examples, the composition is applied (for example, sprayed) on the fruit tree or portion thereof at a rate of at least about 50 gallons/acre (for example, about 75, 100, 125, 150, 175, 200, 225, 250, or more ga/acre).

In some examples, the methods include applying the composition including BABA to the fruit tree or portion of the fruit tree (such as leaves, buds, flowers, branches, or a combination of two or more thereof) during bud or flower development. In some examples, the composition including BABA is applied to the fruit tree or portion thereof during autumn (for example, after leaf drop), during bud development, during flower development (for example prior to full bloom), or a combination of two or more thereof. In other examples, the composition including BABA is applied in the spring (for example during bud or flower development) prior to frost or freezing temperatures, such as about 1-10 days prior to freezing temperatures. For example, the composition including BABA is applied about 1, 2, 3, 4, 5, 6, 7, 8, 9, or 10 days prior to occurrence of freezing temperatures. In some examples, the methods include one or more applications of the composition including BABA (such as 1, 2, 3, 4, 5, or more applications).

In some embodiments, the disclosed methods include applying to a fruit tree or a portion thereof a composition including about 50-750 ppm BABA (such as, but not limited to about 50-500 ppm, 100-300 ppm, 50-200 ppm, or 100-200 ppm). In some examples, the composition includes at least 50 ppm BABA (for example, about 50, 100, 150, 200, 250, 300, 350, 400, 450, 500, 550, 600, 650, 700, or 750 ppm). In a particular example, the composition includes about 100 ppm BABA. In another particular example, the composition includes about 500 ppm BABA.

Cold damage to a fruit tree can be assessed by methods known to one of skill in the art, including but not limited to determining flowers killed, fruit set, fruit size, pistil survival, leaf area, and/or leaf chlorophyll content index. In some examples of the disclosed methods, decreasing cold damage includes decreasing flowers killed after exposure to cold temperature (for example, a temperature of about 0° C. or less), for example decreasing the percentage of flowers killed as compared to a control (such as an untreated or vehicle treated tree or population of trees). For example, decreasing cold damage includes decreasing the percentage of flowers killed on a fruit tree or a portion thereof by at least about 10% (such as, but not limited to about 20%, 30%, 40%, 50%, 60%, 70%, 80%, 90%, 95%, or even more) as compared to a control. In other examples, decreasing cold damage includes having less than 90% of flowers killed (such as, but not limited to less than 80%, 70%, 60%, 50%, 40%, 30%, 25%, 20%, 15%, 10%, or 5% of flowers killed) on a tree or portion of a tree after exposure to cold temperature (for example, a temperature of about 0° C. or less). One of skill in the art can determine if a flower has been killed (for example, by visual assessment for the presence of discolored pistil tissues).

In other examples of the disclosed methods, decreasing cold damage includes increasing fruit set after exposure to cold temperature (for example, a temperature of about 0° C. or less), for example increasing the percentage of flowers which develop into fruit as compared to a control (such as an untreated or vehicle treated tree or population of trees). For example, decreasing cold damage includes increasing the percentage of flowers which develop into fruit on a fruit tree or a portion thereof by at least about 10% (such as, but not limited to about 25%, 50%, 75%, 1.5-fold, 2-fold, 3-fold, 4-fold, 5-fold, 10-fold, or more) as compared to a control. In other examples, decreasing cold damage includes having a fruit set of more than about 30% (such as, but not limited to about 40%, 50%, 60%, 70%, 80%, 90%, 95%, or more) on a tree or a portion of a tree after exposure to cold temperature (for example, a temperature of about 0° C. or less).

In further examples of the disclosed methods, decreasing cold damage includes increasing fruit size after exposure to cold temperature (for example, a temperature of about 0° C. or less), for example increasing the weight, length, width, and/or diameter of fruit as compared to a control (such as an untreated or vehicle treated tree or population of trees). For example, decreasing cold damage includes increasing at least one measure of fruit size by at least about 10% (such as, but not limited to about 25%, 50%, 75%, 1.5-fold, 2-fold, 3-fold, 4-fold, 5-fold, 10-fold, or more) as compared to a control.

In some examples of the disclosed methods, decreasing cold damage includes increasing pistil survival after exposure to cold temperature (for example, a temperature of about 0° C. or less), for example increasing the percentage of surviving pistils as compared to a control (such as an untreated or vehicle treated tree or population of trees). For example, decreasing cold damage includes increasing pistil survival on a fruit tree or a portion thereof by at least about 10% (such as, but not limited to about 20%, 30%, 40%, 50%, 60%, 70%, 80%, 90%, 95%, or even more) as compared to a control. In some examples, pistil survival is determined by visual examination of the pistil tissue (including pistil, style, and/or ovaries/locules). The presence of brown or black tissue on pistil tissue or a portion thereof indicates tissue death (for example, killed by cold damage).

In other examples of the disclosed methods, decreasing cold damage includes increasing leaf size after exposure to cold temperature (for example, a temperature of about 0° C. or less), for example increasing leaf length, width, and/or area as compared to a control (such as an untreated or vehicle treated tree or population of trees). For example, decreasing cold damage includes increasing at least one measure of leaf size by at least about 10% (such as, but not limited to about 25%, 50%, 75%, 1.5-fold, 2-fold, 3-fold, 4-fold, 5-fold, 10-fold, or more) as compared to a control.

In additional examples of the disclosed methods, decreasing cold damage includes increasing leaf chlorophyll content after exposure to cold temperature (for example, a temperature of about 0° C. or less), for example increasing leaf chlorophyll content index as compared to a control (such as an untreated or vehicle treated tree or population of trees). In other examples, decreasing cold damage includes increasing chlorophyll fluorescence after exposure to cold temperature (for example, a temperature of about 0° C. or less), for example increasing chlorophyll fluorescence as compared to a control (such as an untreated or vehicle treated tree or population of trees). For example, decreasing cold damage includes increasing at least one measure of leaf chlorophyll content by at least about 10% (such as, but not limited to about 25%, 50%, 75%, 1.5-fold, 2-fold, 3-fold, 4-fold, 5-fold, 10-fold, or more) as compared to a control.

For the purposes of determining cold damage to a fruit tree, one or more trees or a portion of one or more trees can be used. Parameters that reflect cold damage (for example, flowers killed, fruit set, pistil survival, fruit size, leaf size, and/or leaf chlorophyll content) can be determined using routine methods. The parameter can be assessed in the treated tree (or portion thereof) and optionally in a control tree (or portion thereof) or an untreated portion of the treated tree. The parameter in the treated tree can be compared to the same parameter in an untreated tree or other control (such as a standard value or reference value). In some examples, the increase or decrease in the measured parameter is a significant (for example, statistically significant) increase or decrease. A significant increase or decrease in the parameter can be evaluated using statistical methods known in the art.

IV. Methods of Increasing Fruit Set, Fruit Size, and Fruit Quality

Disclosed herein are methods for increasing one or more aspects of fruit production by a fruit tree, including fruit set, fruit size, and fruit quality (such as one or more of fruit firmness, sweetness, color, total soluble content, and storability). In some embodiments, the methods include applying a composition including one or more plant growth regulators to a fruit tree.

A. Prohexadione-Calcium

In some embodiments, the disclosed methods include increasing fruit size, fruit quality, or a combination thereof of fruit from a fruit tree. The methods include applying to the fruit tree (or a portion thereof) an effective amount of a composition including PCa or PCa and one or more gibberellins (such as GA1, GA3, GA4, GA7, or a combination of two or more thereof). In particular examples, the methods include applying to the fruit tree an effective amount of a composition including PCa and GA3 or a composition including PCa and a combination of GA4 and GA7 (GA4/7). In some examples, GA4/7 includes a mixture of about 70:30 GA4:GA7.

In some embodiments, the methods include applying the composition to fruit tree leaves, buds, flowers, branches, or a combination of two or more thereof. In particular examples, the composition is applied to the tree by spraying, for example spraying with a solution including PCa or PCa and one or more gibberellins. In some examples, the composition is applied (for example, sprayed) on the fruit tree or portion thereof until it runs off the tree (for example, the leaves, buds, flowers, and/or branches). In other examples, the composition is applied (for example, sprayed) on the fruit tree or portion thereof at a rate of at least about 50 gallons/acre (for example, about 75, 100, 125, 150, 175, 200, 225, 250, or more ga/acre). In some examples, the methods include applying the composition including PCa or PCa and one or more gibberellins to the fruit tree or portion of the fruit tree (such as leaves, buds, flowers, branches, or a combination of two or more thereof) during fruit development.

In some examples, the composition is applied to the fruit tree or portion thereof between about day 20 to day 40 after anthesis (such as about day 20, 21, 22, 23, 24, 25, 26, 27, 28, 29, 30, 31, 32, 33, 34, 35, 36, 37, 38, 39, or 40 after anthesis). In a particular example, the composition including PCa or PCa and one or more gibberellins is applied to the fruit tree at about day 30 after anthesis. In another particular example, the composition including PCa or PCa and one or more gibberellins is applied to the fruit tree at about day 37 after anthesis.

One of skill in the art can identify when anthesis (full flower opening) occurs. In some examples, anthesis is the time of opening of a flower bud (for example, when a flower becomes accessible to a pollinator). Anthesis is determined on a bud-by-bud basis. However, in some non-limiting examples, it is determined for a tree as a point when a particular number or percentage of flower buds on the tree have opened, for example, more than about 50% of flower buds opened (such as, but not limited to about 60%, 65%, 70%, 75%, 80%, 85%, 90%, 95%, or more of flower buds opened). In one example, anthesis refers to full bloom of a tree, for example, the time when all or substantially all flowers on the tree have opened.

In other examples, the composition is applied to the fruit tree or portion thereof during stage II of fruit development. One of skill in the art can identify the stage of fruit development for a particular type of fruit. For example, stone fruit crops have three stages of fruit development: stage I, characterized by an increase in number and size of seed and mesocarp cells; stage II, differentiation of the endocarp and pit hardening with little radial expansion; and stage III, expansion of the mesocarp from cell expansion (see, e.g., Westwood, *Temperate-Zone Pomology: Physiology and Culture*, $3^{rd}$ ed., Timber Press, 2003). In some examples, stage I lasts until the pit hardens (for example, tested by cutting through fruitlets), stage II last until a color change from green to yellow, and stage III lasts until harvest.

In some examples, the methods include one or more applications of the composition including PCa or PCa and one or more gibberellins (such as 1, 2, 3, 4, 5, or more applications).

In some embodiments, the disclosed methods include applying to a fruit tree or a portion thereof a composition including about 50-300 mg/L PCa (such as, but not limited to about 100-300 mg/L, about 50-250 mg/L, about 100-200 mg/L, or about 150 mg/L). In a particular example, a composition including about 150 mg/L PCa is applied to the fruit tree. In other embodiments, the disclosed methods include applying to a fruit tree or a portion thereof a composition including about 50-300 mg/L PCa (such as, but not limited to about 100-300 mg/L, about 50-250 mg/L, about 100-200 mg/L, or about 150 mg/L) and about 10-50 mg/L (such as, but not limited to about 10-40 mg/L, about 10-30 mg/L, about 20-40 mg/L, or about 30 mg/L) of one or more gibberellins. In one particular example, the methods include applying to a fruit tree a composition including about 150 mg/L PCa and about 30 mg/L GA3. In another particular example, the methods include applying to a fruit tree a composition including about 150 mg/L and about 30 mg/L GA4/7 (such as, but not limited to 70:30 GA4:GA7).

Fruit size can be assessed by methods known to one of skill in the art, including but not limited to determining fruit weight, fruit length, fruit width, fruit diameter, or a combination of two or more thereof. In some examples of the disclosed methods, increasing fruit size includes increasing fruit weight (for example, average fruit weight) by at least about 5% (such as, but not limited to about 10%, 15%, 20%, 25%, 50%, 75%, 1.5-fold, 2-fold, 3-fold, 4-fold, 5-fold, 10-fold, or more) as compared to a control. In other examples, the percentage of fruit in a particular weight range is increased by at least about 5% (such as, but not limited to about 10%, 15%, 20%, 25%, 50%, 75%, 1.5-fold, 2-fold, 3-fold, 4-fold, 5-fold, 10-fold, or more) as compared to a control. One of skill in the art can determine appropriate weight ranges for a given fruit. For example, exemplary weight ranges for cherries are less than 6 g, 6-7 g, 7-8 g, 8-9 g, 9-10 g, and greater than 10 g. In a particular example, the percentage of cherries weighing greater than 10 g is increased as compared to a control.

In other examples, increasing fruit size includes increasing one or more of fruit length, fruit width, or fruit diameter (such as average length, width, and/or diameter) by at least about 5% (such as, but not limited to about 10%, 15%, 20%, 25%, 50%, 75%, 1.5-fold, 2-fold, 3-fold, 4-fold, 5-fold, 10-fold, or more) as compared to a control. In further examples, increasing fruit size includes increasing row size (for example, average row size) by at least 5% (such as, but not limited to about 10%, 15%, 20%, 25%, 50%, 75%, 1.5-fold, 2-fold, 3-fold, 4-fold, 5-fold, 10-fold, or more) as compared to a control. One of skill in the art can determine row size by routine methods, for example, using a sizing chart or sizer rings.

Fruit quality can be assessed by methods known to one of skill in the art, including but not limited to determining fruit firmness, fruit total soluble solid content, fruit acidity, fruit color, fruit storability, fruit sensory attributes, or a combination of two or more thereof. In some examples of the disclosed methods, increasing fruit quality includes increasing fruit firmness (for example, average fruit firmness) by at least about 5% (such as, but not limited to about 10%, 15%, 20%, 25%, 50%, 75%, 1.5-fold, 2-fold, 3-fold, 4-fold, 5-fold, 10-fold, or more) as compared to a control. Fruit firmness can be determined by methods known to one of skill in the art, for example, utilizing a fruit firmness tester (such as FirmTech 2, BioWorks, Inc., Wamego, Kans.) or the Magness-Taylor firmness test.

In further examples, increasing fruit quality includes increasing fruit juice total soluble solid content, pH, and/or titratable acidity by at least about 5% (such as, but not limited to about 10%, 15%, 20%, 25%, 50%, 75%, 1.5-fold, 2-fold, 3-fold, 4-fold, 5-fold, 10-fold, or more) as compared to a control. One of skill in the art can determine soluble solids, for example utilizing a refractometer. Likewise, one of skill in the art can determine juice pH and titratable acidity, for example utilizing a pH meter or titrator.

In still further examples, increasing fruit quality includes increasing fruit color, for example by increasing the percentage of fruit at a particular color by at least about 5% (such as, but not limited to about 10%, 15%, 20%, 25%, 50%, 75%, 1.5-fold, 2-fold, 3-fold, 4-fold, 5-fold, 10-fold, or more) as compared to a control. Methods for assessing fruit color are known to one of skill in the art. In some examples, color sorting is carried out with color comparators developed by CTIFL (Centre Technique Interprofessionnel des Fruit et Legumes), which categorizes color into eight levels from green, CTIFL 1 to CTIFL 7.

In other examples, increasing fruit quality includes increasing fruit storability (for example, shelf life) by at least about 5% (such as, but not limited to about 10%, 15%, 20%, 25%, 50%, 75%, 1.5-fold, 2-fold, 3-fold, 4-fold, 5-fold, 10-fold, or more) as compared to a control. In some examples, fruit storability is assessed by rating fruit by the degree of decay following a period of storage (for example, storage at room temperature or under refrigeration, such as about 4° C.). In some examples, fruit is stored for at least 3 days (such as, but not limited to at least 5, 7, 10, 14, 21, 28, 30, 45, 60, or more days). In one example, fruit is rated according to degree of decay and surface pitting into at least four groups: 0, healthy and free of defects; 1, partial decay or pitting; 2, around 50% decay or pitting; and 4, more than 50% decay and pitting. In some examples, the disclosed methods increase the percentage of fruit in categories 0 and/or 1 after storage, as compared to a control. In further examples, fruit storability is assessed by measuring fruit firmness and/or other fruit quality attributes, as described herein. In some examples, the disclosed methods increase the firmness of fruit after storage, as compared to a control. In further examples, the disclosed methods increase total soluble solid content, pH, titratable acidity, fruit color, sensory attributes, or a combination of two or more thereof after storage, as compared to a control. In additional examples, fruit storability is assessed by determining the percentage of fruit with a particular visual characteristic, for example fruit with a green pedicel, for cherries. In some examples, the disclosed methods increase the percentage of cherries with a green pedicel after storage as compared to a control.

In further examples, fruit quality includes sensory attributes (for example, overall appearance, firmness, sweetness, tartness, flavor, and overall acceptance). Sensory attributes are expressed on a relative scale (for example, from 0 to 10, where 0 represents the worst and 10 represents the best) as evaluated by one or more individuals. In some embodiments, increasing fruit quality includes increasing a rating of one or more sensory attributes (for example, increasing the rating by at least one numerical value or step) as compared to a control. In some examples, one or more sensory attributes are increased after storage, for example, as compared to a control.

For the purposes of determining fruit size or fruit quality, fruit from one or more trees or a portion of one or more trees can be used (for example fruit from a treated tree or portion thereof and optionally fruit from a control tree or portion thereof). Parameters that reflect fruit size (such as fruit weight, fruit length, fruit width, and/or fruit diameter) or fruit quality (such as fruit firmness, fruit total soluble solid content, fruit color, fruit storability, and/or fruit sensory attributes) can be determined using routine methods. The parameter can be assessed in fruit from the treated tree (or portion thereof) and optionally in from fruit from a control tree (or portion thereof) or an untreated portion of the treated tree. The parameter determined for fruit from the treated tree can be compared to the same parameter in fruit from an untreated tree or other control (such as a standard value or reference value). In some examples, the increase or decrease in the measured parameter is a significant (for example, statistically significant) increase or decrease. A significant increase or decrease in the parameter can be evaluated using statistical methods known in the art.

B. 4-Chlorophenoxyacetic Acid

In some embodiments, the disclosed methods include increasing fruit size, fruit set, or a combination thereof of a fruit tree. The methods include applying to the fruit tree (or a portion thereof) an effective amount of a composition including CPA.

In some embodiments, the methods include applying the composition to fruit tree leaves, buds, flowers, branches, or a combination of two or more thereof. In particular examples, the composition is applied to the tree by spraying, for example spraying with a solution including CPA. In some examples, the composition is applied (for example, sprayed) on the fruit tree or portion thereof until it runs off the tree (for example, the leaves, buds, flowers, and/or branches). In other examples, the composition is applied (for example, sprayed) on the fruit tree or portion thereof at a rate of at least about 50 gallons/acre (for example, about 75, 100, 125, 150, 175, 200, 225, 250, or more ga/acre). In some examples, the methods include applying the composition including CPA to the fruit tree or portion of the fruit tree (such as leaves, buds, flowers, branches, or a combination of two or more thereof) during flowering (including but not limited to first opening, full bloom, or a combination thereof) or post-bloom. In a particular example, the composition including CPA is applied to the fruit tree or portion thereof at full bloom. In other examples, the composition including CPA is applied to the fruit tree when there are open flowers on the tree. In a further example, the composition including CPA is applied to the fruit tree or portion thereof about 1-10 days post-bloom (such as about 1, 2, 3, 4, 5, 6, 7, 8, 9, or 10 days post-bloom). One of skill in the art can identify when flowering occurs. In some examples, flowering of a tree includes at least about 10% open flowers (such as, but not limited to about 20%, 30%, 40%, 50%, 60%, 70%, 80%, 90%, 95%, or more open flowers). In some examples, the methods include one or more applications of the composition including CPA (such as 1, 2, 3, 4, 5, or more applications). In one particular example, the composition including CPA is applied to a fruit tree or portion thereof at about 50% bloom and at full bloom.

In some embodiments, the disclosed methods include applying to a fruit tree or a portion thereof a composition including about 10-100 mg/L CPA (such as, but not limited to about 10-75 mg/L, about 25-50 mg/L, about 10-50 mg/L, or about 30 mg/L). In a particular example, a composition including about 30 mg/L CPA is applied to the fruit tree. In other examples, a composition including about 10 mg/L CPA is applied to the fruit tree. In still further examples, a composition including about 100 mg/L CPA is applied to the fruit tree.

Fruit size can be assessed by methods known to one of skill in the art, including but not limited to determining fruit weight, fruit length, fruit width, fruit diameter, or a combination of two or more thereof. In some examples of the disclosed methods, increasing fruit size includes increasing fruit weight (for example, average fruit weight) by at least about 5% (such as, but not limited to about 10%, 25%, 50%, 75%, 1.5-fold, 2-fold, 3-fold, 4-fold, 5-fold, 10-fold, or more) as compared to a control. In other examples, the percentage of fruit in a particular weight range is increased by at least about 5% (such as, but not limited to about 10%, 25%, 50%, 75%, 1.5-fold, 2-fold, 3-fold, 4-fold, 5-fold, 10-fold, or more) as compared to a control. One of skill in the art can determine appropriate weight ranges for a given fruit. For example, exemplary weight ranges for cherries are less than 6 g, 6-7 g, 7-8 g, 8-9 g, 9-10 g, and greater than 10 g. In a particular example, the percentage of cherries weighing greater than 10 g is increased as compared to a control.

In other examples, increasing fruit size includes increasing one or more of fruit length, fruit width, or fruit diameter (such as, but not limited to average length, width, and/or diameter) by at least about 5% (such as, but not limited to about 10%, 25%, 50%, 75%, 1.5-fold, 2-fold, 3-fold, 4-fold, 5-fold, 10-fold, or more) as compared to a control. In further examples, increasing fruit size includes increasing row size (for example, average row size) by at least 5% (such as, but not limited to about 10%, 15%, 20%, 25%, 50%, 75%, 1.5-fold, 2-fold, 3-fold, 4-fold, 5-fold, 10-fold, or more) as compared to a control. One of skill in the art can determine row size by routine methods, for example, using a sizing chart or sizer rings.

Fruit set can be assessed by methods known to one of skill in the art. In some examples of the disclosed methods, increasing fruit set includes increasing percentage of flowers developing into fruit by at least about 5% (such as, but not limited to about 10%, 25%, 50%, 75%, 1.5-fold, 2-fold, 3-fold, 4-fold, 5-fold, 10-fold, or more) as compared to a control. In some examples, fruit set includes initial fruit set (such as percentage or proportion of flowers developing into fruitlets), final fruit set (such as percentage or proportion of flowers developing into mature fruit), or a combination thereof. In some examples, fruit set is determined on one or more selected branches or limbs of one or more trees. For example, fruit set can be assessed by counting total flowers on a representative tree limb and counting the number of fruit on the limb at later time points, for example every week, or at harvest. Fruit set is expressed as fruit per available flowers.

For the purposes of determining fruit size or fruit set, one or more trees or a portion of one or more trees can be used. Parameters that reflect fruit size (for example, fruit weight, fruit length, fruit width, and/or fruit diameter) or fruit set (for example, percentage of flowers that start developing into fruit and/or percentage of flowers that become mature fruit) can be determined using routine methods. The parameter can be assessed in the treated tree (or portion thereof) and optionally in a control tree (or portion thereof) or an untreated portion of the treated tree. The parameter determined for the treated tree can be compared to the same parameter in an untreated tree or other control (such as a standard value or reference value). In some examples, the increase or decrease in the measured parameter is a significant (for example, statistically significant) increase or decrease. A significant increase or decrease in the parameter can be evaluated using statistical methods known in the art.

V. Fruit Trees

The methods disclosed herein can be used to improve aspects of fruit production and fruit quality in various fruit trees. In some embodiments, the fruit tree is a stone fruit tree, including, but not limited to sweet cherry (e.g., *Prunus avium*), tart ("sour" or "pie") cherry (e.g., *Prunus cerasus*), plum (e.g., *Prunus domestica, Prunus salicina*, or *Prunus insititia*), peach (e.g., *Prunus persica*), nectarine (e.g., *Prunus persica* var. *nucipersica*), or apricot (e.g., *Prunus armeniaca*) tree. In particular examples, the fruit tree is a sweet cherry (*Prunus avium*) cultivar, such as 'Bing,' 'Chelan,' 'Van,' 'Tieton,' 'PC 8011-3,' 'Regina,' 'Rainier,' 'Chinook,' 'Lambert,'' Compact Lambert,' 'Corum,' 'Emperor Francis,' Gold,' 'Napoleon' (also known as 'Royal Ann' or 'Queen Ann'), 'Hedelfingen,' 'Hudson,' 'Sam,' 'Schmidt,' 'Stella,' 'Sweetheart,' 'Ulster,' 'Vista,' 'Windsor,' 'Bada,' 'Sweet Ann,' 'Vega,' 'Black Republican,' 'Black Tartarian,' 'Cavalier,' 'Early Burlat,' 'Hardy Giant,' 'Kristin,' 'Summit,' 'Utah Giant,' 'Valera,' 'Venus,' 'Viscount,' 'Viva,' 'Vogue,' 'Lapins,' 'Attika,' 'Sunburst,' or 'Starkrimson.' In other examples, the fruit tree is a tart (sour) cherry (*Prunus cerasus*) cultivar, such as 'Montmorency,' 'Meteor,' 'Northstar,' 'English Morello,' 'Kentish Red,' 'Amarelles,' 'Griottes,' 'Flemish,' or 'Schattenmorelle.' In some examples, the fruit tree is a plum (*Prunus domestica, Prunus salicina*, or *Prunus insititia*) cultivar, such as 'PP 7524-7,' 'Reine Claude,' 'Imperial Gage,' 'Hand,' 'Yellow egg,' 'Golden drop,' 'Victoria,' 'Lombard,' 'Pond,' 'French,' 'Stanley,' 'Italian,' 'Blufre,' 'President,' 'Santa Rosa,' 'Burbank,' 'Shiro,' 'Beauty,' 'Gold,' 'Methley,' 'Hollywood,' 'Red Beaut,' 'Ozark Premier,' 'Friar,' or 'Simka.' In further examples, the fruit tree is a peach (*Prunus persica*) cultivar, such as 'Redhaven,' 'Glohaven,' 'Red Globe,' 'Canadian Harmony,' 'Elberta' (including 'Early Elberta,' 'Fantastic Elberta,' or 'July Elberta'), 'Veteran,' 'Reliance,' 'Harken,' 'Polly,' 'Ranger,' 'Sweet Sue,' 'Harbelle,' 'Starfire,' or 'Frost.' In additional examples, the fruit tree is a nectarine (*Prunus persica* var. *nucipersica*) cultivar, such as 'Hardired,' 'August Red,' 'September Red,' 'Spring Bright,' 'Summer Fire,' 'Early Diamond,' 'Spring Diamond,' 'Red Diamond,' 'Big Juan,' 'Early May,' 'May Grand,' 'Arctic Snow,' or 'Arctic Glow.' In other examples, the fruit tree is an apricot (*Prunus armeniaca*) cultivar, such as 'Puget Gold,' 'Harglow,' 'Westley,' 'Goldrich,' 'Goldbar,' 'Goldstrike,' 'Hargrand,' 'Pui-Sha-Sin,' 'Reliable,' 'Skaha,' 'Sundrop,' 'Tilton,' 'Tomcat,' or 'Wenatchee.' One of skill in the art can identify other suitable stone fruit species or cultivars or strains thereof for use in the methods disclosed herein.

In other embodiments, the fruit tree is a pome fruit tree, including, but not limited to apple (e.g., *Malus domestica*), pear (e.g., *Pyrus communis* or *Pyrus pyrifolia*), quince (e.g., *Cydonia oblonga*), or loquat (e.g., *Eriobotrya japonica*) tree. In some examples, the fruit tree is an apple (*Malus domestica*) cultivar, such as 'Fuji,' 'Red Delicious,' 'Golden Delicious,' 'Gala,' 'Honeycrisp,' 'Jonagold,' 'Jonathan,' 'MacIntosh,' 'Empire,' 'Cortland,' 'Braeburn,' 'Gravenstein,' 'Baldwin,' 'Newtown Pippn,' 'Granny Smith,' 'Cripps Pink,' Cameo, 'Rome,' 'Winesap,' 'Ginger Gold,' or strains thereof. In other examples, the fruit tree is a pear (*Pyrus communis*) cultivar, such as 'Anjou,' 'Bosc,' 'Bartlett,' 'Comice,' 'Seckel,' 'Concorde,' or 'Conference.' In other examples, the fruit tree is an Asian pear (*Pyrus pyrifolia*) cultivar, such as 'Hamese,' 'Shinseiki,' 'Kosui,' 'Mishirasu,' 'Chojuro,' or 'Atago.' In some examples, the fruit tree is a quince (*Cydonia oblonga*) cultivar, such as 'Champion, 'Smyrna,' 'Aromatnaya,' 'Carps Sweet Quince,' 'Cathay Quince,' 'Orange,' or 'Portugal.' In further examples, the fruit tree is a loquat (*Eriobotrya japonica*) cultivar, such as 'Advance,' 'Champagne,' 'Premier,' 'Victor,' 'Early Red,' or 'Tanaka.' One of skill in the art can identify other suitable pome species or cultivars or strains thereof for use in the methods disclosed herein.

VI. Formulations and Methods of Application

The methods disclosed herein utilize compositions which include BABA, PCa, gibberellins, and/or CPA. Compositions including these compounds can be formulated using routine methods in the art. For example, the compounds can be formulated with agriculturally acceptable carriers or diluents. Agriculturally acceptable carriers include adjuvants, mixers, enhancers, or combinations thereof suitable for application of the composition. Examples of suitable liquid agriculturally acceptable carriers include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, and glycerine. Exemplary solid agriculturally acceptable carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, and lignin. Additional adjuvants include antifoam agents, neutralizing agents, buffers, dispersing agents, thickening agents, sequestering agents, and so on.

The compositions may include one or more compounds in the form of an agriculturally acceptable salt. Agriculturally acceptable salts include salts, the cations or anions of which are known and accepted in the art for the formation of salts for agricultural or horticultural use. Preferably the salts are water-soluble. Suitable salts with bases include alkali metal (such as sodium and potassium), alkaline earth metal (such as calcium and magnesium), ammonium and amine (for example, diethanolamine, triethanolamine, octylamine, morpholine and dioctylmethylamine) salts. Suitable acid addition salts include salts with inorganic acids, for example hydrochlorides, sulfates, phosphates and nitrates and salts with organic acids, for example acetic acid.

In some examples, the concentration of the active ingredients in the composition (for example, BABA, PCa, GA, CPA, or a combination thereof) is about 0.001 to about 98% by weight (for example, about 0.01 to 90% by weight). In compositions designed to be employed as concentrates, the active ingredient is generally present in a concentration from about 5 to about 98 weight %, such as, but not limited to about 10 to 90 weight %. Such compositions can be diluted with a carrier, such as water, before application Particular formulations to be applied in spraying forms, such as water dispersible concentrates or wettable powders, may contain surfactants, such as wetting and dispersing agents, e.g., the condensation product of formaldehyde with naphthalene sulfonate, an alkyl-aryl-sulfonate, a lignin sulfonate, a fatty alkyl sulfate, an ethoxylated alkylphenol or an ethoxylated fatty alcohol.

In some examples, the compounds included in the compositions disclosed herein are in either solid or liquid application forms, such as in the form of a wettable powder, an emulsion concentrate, a water dispersible suspension concentrate ("flowable"), a dusting powder, a granulate, a delayed release form incorporating conventional carriers, diluents and/or adjuvants. Such compositions may be produced in any conventional manner, for example, by mixing the active ingredient with a carrier and other formulating ingredients.

In further examples, the compositions disclosed herein also include one or more other agents useful in fruit production, for example, one or more fungicide, herbicide, pesticide, or a combination of two or more thereof. The compositions can also be applied in combination with one or more other agents useful in fruit production for example, one or more fungicide, herbicide, pesticide, or a combination of two or more thereof. The term "application in combination" or "co-application" refers to both concurrent and sequential application of the active agents.

The following examples are provided to illustrate certain particular features and/or embodiments. These examples should not be construed to limit the invention to the particular features or embodiments described.

EXAMPLES

Example 1

Decreasing Cold Damage in Tree Fruit

This example describes frost protection in tree fruit utilizing DL-β-aminobutyric acid (BABA).

Sweet cherry cv. 'Bing' trees were sprayed in the field with BABA and the fate of flowers from randomly selected sample limbs placed in a programmable freeze chamber was evaluated. Random limbs were removed from the freeze chamber within 10 minutes of reaching selected air temperatures, and were left at room temperature for 1 hour. Pistil/ovary survival was then assessed visually on every flower. Flowers with healthy green stylar and ovary tissue were rated as live. Flowers with discolored (for example, brown) stylar or ovary tissues were rated as dead. Fruit set, fruit size, average leaf area, and leaf chlorophyll content index were evaluated on other limbs of the treated trees.

Treatment with 100 ppm BABA decreased the percentage of flowers killed at both −3.5° C. and −4.5° C. as compared to control (untreated) trees (FIG. 1A). Treatment with 500 ppm BABA also decreased the percentage of flowers killed (FIG. 1A). Treatment with BABA at both concentrations also increased fruit set, fruit size, average leaf area, and leaf chlorophyll content index as compared to control (FIGS. 1B-E).

BABA was also applied to 'Fuji' apple trees at different bud development stages. Five days later, treated and untreated (control) branches were collected and placed in a programmable freeze chamber. Flowers killed were evaluated as described above. BABA decreased the percentage of flowers killed as compared to control at all developmental stages, except for full opened flowers (FIG. 2).

Figure 3:
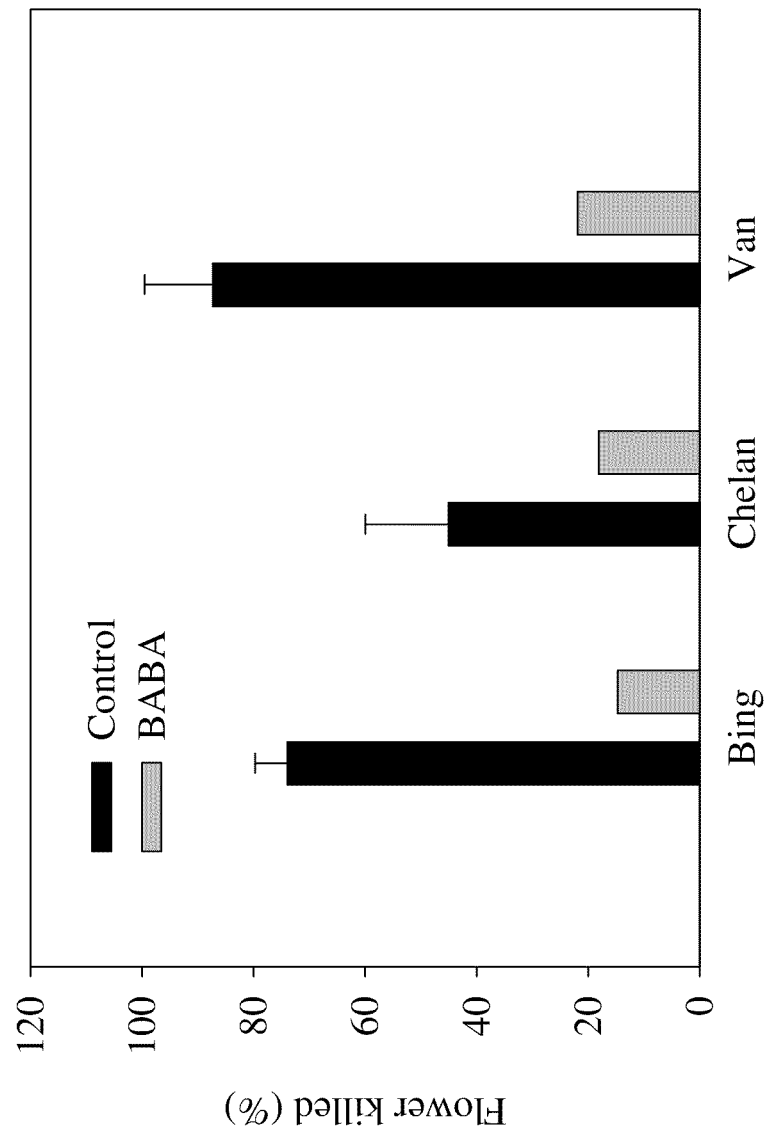
FIG. 3 is a graph showing flower fate of the indicated sweet cherry cultivars after autumn application of BABA and following natural spring frost damage.
Figure 4:
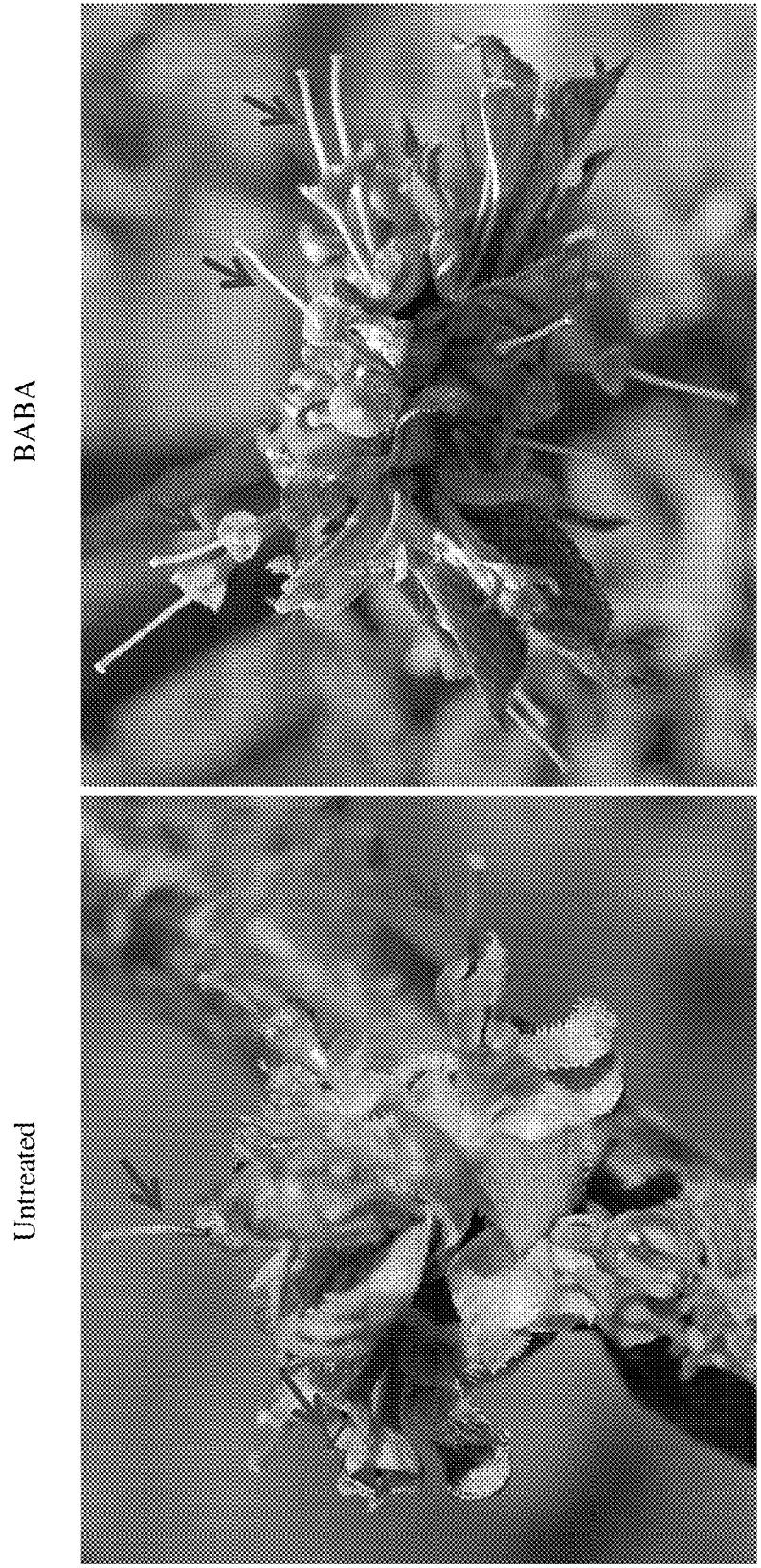
FIG. 4 is a pair of digital images showing pistil survival in sweet cherry cv. 'Bing' after autumn application of BABA and following spring frost damage. Left, control (untreated) branch; right, BABA-treated branch. Arrows indicate the pistil base. Pistils on the untreated branch were discolored at the base, indicating that the pistil was dead.

Application of BABA to sweet cherry cultivars 'Bing,' 'Chelan,' and 'Van' in autumn decreased the percentage of flowers killed after natural frost damage the following spring (FIG. 3). Autumn application of BABA also increased pistil survival in sweet cherry cv. Bing after spring frost damage (FIG. 4).

Figure 5:
FIG. 5 is a pair of digital images showing fruit set in plum cv. 'PP7524-7' after application of BABA about 4-7 days prior to frost. Left, control (untreated) branch; right, BABA-treated branch.

Finally, BABA application in the spring 4-7 days prior to frost exposure increased fruit set in plum cv. 'PP7524-7' following spring frost damage (FIG. 5).

Example 2

Increasing Fruit Size and Fruit Quality in Tree Fruit

This example describes increasing fruit size, fruit yield, and fruit quality in tree fruit utilizing prohexadione-calcium (PCa) alone or in combination with gibberellins.

Materials and Methods

A limb trial was conducted to evaluate effects of bioactive gibberellins (GA), prohexadione-calcium (PCa), or combinations applied before harvest on fruit quality of sweet cherry. The most efficacious treatments were utilized in a larger scale trial to investigate their effects on the whole tree scale and postharvest characteristics of fruit. Twelve-year-old sweet cherry cv 'Bing' on 'Gisela® 1' rootstock was selected for both experiments and trained to a central leader architecture. Both trials were carried out at Washington State University Roza farm, Prosser, Wash., USA (N 46.2°, W 119.7°).

Experiment 1

Three limbs with uniform vigor were selected from each of 10 trees. Treatments were applied to the limbs randomly spread across ten trees at 30 days after anthesis, approximately coinciding with the onset of pit hardening (stage II of fruit development) in 'Bing'. The experiment consisted of 10 treatments, including water (the untreated control) and PCa at 150 mg/L. Bioactive $GA_1$, $GA_3$, and $GA_{4/7}$ (70:30 $GA_4$:$GA_7$) were applied as a foliar spray at 30 mg/L alone or in combination with PCa at 150 mg/L. In addition, the combination of $GA_3$ and $GA_{4/7}$ at 30 mg/L was applied, or in combination with PCa at 150 mg/L. PCa was the commercial product Apogee® (27.5% PCa; BASF Corp., Research Triangle Park, N.C.) and all bioactive GAs (purity >90%) were purchased from OlChemIm Ltd. (Olomouc, Czech Republic). Each treatment was made with a pressurized handgun sprayer to entire limbs, ceasing at the first runoff.

Twenty fruit per treatment were randomly selected and flagged for monitoring fruit growth by measuring fruit equatorial diameter and height weekly after treatment. All current-season shoots on treated limbs were measured weekly to investigate treatment effects on shoot growth. Harvest timing was determined as the day when the majority of fruit had achieved commercial maturity, based on exocarp color. At harvest, all fruit on treated limbs were harvested and transported to the laboratory for fruit quality analysis. Floral bud density on the treated limbs was assessed by counting all spurs and the number of reproductive buds per spur.

Experiment 2

Experiment 2 included treatments at the whole tree level. Applications of $GA_3$ or $GA_{4/7}$ (70:30 $GA_4$:$GA_7$) were made to entire trees at 30 mg/L in combination with PCa at 150 mg/L. PCa (150 mg/L) alone was also applied and an untreated control treatment was included. To investigate the role of application timing of plant growth regulators, all treatments were applied at 30 (first spray (FS)) or 37 days after anthesis (second spray (SS)). In this experiment, 24 trees in the same orchard as those in Experiment 1 were selected for whole tree treatment and assigned randomly into one of two 12-tree groups for the timing study. Treatments were then randomly assigned to each of three trees per application timing. Treatments were applied to entire trees by pressurized handgun sprayer to the point of first runoff. All applications were completed in the morning between 0800 and 1100, and applied on days with little or no wind. To prevent spray drift onto neighboring experimental units, all the trees were selected in the same row and 2-3 trees were selected as 'border' trees between experimental units.

Twenty fruit per treatment were marked for weekly fruit size measurement, and six current terminal shoots were selected for monitoring shoot growth weekly after treatment. The fruit were harvested for crop yield evaluation 42 days after FS (35 days after SS) as the control fruit reached commercial maturity color. Whole tree yield was determined at harvest, in the field, with a portable digital scale. The effect of treatment on total yield per tree (kg tree$^{-1}$) and the yield of large fruit (29.8 mm+) (kg tree$^{-1}$) was assessed. Three sub-samples consisting of 250-300 fruits from each tree were sampled for further fruit quality analysis, storability evaluation and sensory quality study.

Fruit Quality Analysis.

All fruit from each limb in Experiment 1 and sub-samples from Experiment 2 were weighed individually and fruit size distribution was calculated according to fruit weight. Color sorting was conducted manually according to the color comparators developed by CTIFL (Centre Technique Interprofessionnel des Fruit et Legumes, France), which categorize cherry color into 8 levels from Green, CTIFL 1 to CTIFL 7. Fruit number in each category was counted and color distribution was assessed. Subsequently, all fruit were analyzed for firmness and row size measurement with a FirmTech 2 (Bio-Works, Inc, Wamego, Kans.) at room temperature. Then, 25 fruit were randomly selected and 5 groups of 5 fruit were mixed for soluble solids content, pH and titratable acidity measurement. Fruit soluble solids were measured using a digital refractometer (Atago, Japan). Approximately 0.5 mL of juice was dropped directly onto the surface of the refractometer and the measurement immediately taken. Juice pH and titratable acidity were measured with a Mettler DL12 Titrator (Mettler-Toledo, Columbus, Ohio).

Storability Evaluation.

To assess relative differences in shelf life among treatments in Experiment 2, 100 randomly selected fruit were placed in paper bags and kept in refrigerated (4° C.) storage after fruit quality analyses. The fruit were removed after 30 days for quality evaluation. Each fruit was examined and categorized into one of 4 groups, according to the degree of decay and pitting on fruit surface: healthy and free of defects (0); partly decay or pitting (1); around 50% decay or pitting (2); and more than 50% decay or pitting (3). The fruit in each category were counted and the percentage of each category was calculated. The pedicel status was also investigated and the fruit with commercial (green color, turgid) pedicels were counted for each treatment. Furthermore, fruit from category 0 and 1 were subjected to firmness testing, as above. Finally, the fruit in category 0 were used for sensory taste study.

Sensory Analysis.

A study of the effects of the application of plant growth regulators on fruit sensory taste quality after 30 days of storage at 4° C. was conducted. Ten individuals assessed sensory attributes of the stored fruit. Each panelist was presented with 16 fruit (8 cups of two fruit each). Each cup contained two fruit from the same treatment and the treatments were sampled by each panelist in duplicate. Cups were labeled 1 through 8 and each treatment was randomly assigned to two cups for each panelist. The sensory attributes evaluated by panelists included overall appearance, firmness, sweetness, tartness, cherry flavor, and overall acceptance. Results were expressed on a relative scale from 0 to 10, where 0 represents the worst and 10 represents the best.

Statistical Analysis.

All trials were established as randomized complete-block designs. All data were subjected to analysis of variance using the General Linear Models (GLM) program of the SAS statistical analysis package (SAS Institute, Cary, N.C.). Duncan's new multiple range test was used to compare treatments when ANOVA showed significant differences between means.

Results

Experiment 1

In the limb trial, single applications of various GAs (30 mg/L) alone at 30 days after anthesis (early stage II of fruit development, about 17 days before standard GA application timing) did not increase fruit weight compared with the untreated control (Table 1). However, fruit from limbs treated with $GA_3$ plus $GA_{4/7}$ were 10% heavier than those from untreated limbs. PCa (150 mg/L) alone had no positive effect on fruit size.

TABLE 1

Effect of PCa and GAs alone or in combination applied at 30 days after anthesis of 'Bing' sweet cherry.

| Treatment | Fruit weight (g) | Fruit diameter (mm) | Firmness (g/mm) | TSS (Brix) |
|---|---|---|---|---|
| Control | $8.17^{cd}$ | $26.13^{cd}$ | $249.4^e$ | $17.50^{ef}$ |
| PCa | $7.26^f$ | $24.75^f$ | $278.3^c$ | $19.18^{cd}$ |
| $GA_1$ | $8.44^{bc}$ | $26.52^{bc}$ | $280.2^c$ | $20.84^b$ |
| $GA_3$ | $8.23^{cd}$ | $26.49^{bc}$ | $316.9^a$ | $22.23^a$ |
| $GA_{4/7}$ | $8.08^d$ | $26.06^d$ | $262.9^d$ | $18.64^{cd}$ |
| $GA_3 + GA_{4/7}$ | $8.75^{ab}$ | $26.94^a$ | $278.5^c$ | $18.73^{cd}$ |
| PCa + $GA_1$ | $7.69^e$ | $25.62^e$ | $302.7^b$ | $17.45^f$ |
| PCa + $GA_3$ | $8.76^a$ | $26.65^{ab}$ | $281.2^c$ | $18.59^{cde}$ |
| PCa + $GA_{4/7}$ | $8.98^a$ | $26.98^a$ | $284.2^c$ | $18.46^{def}$ |
| PCa + $GA_3 + GA_{4/7}$ | $8.43^c$ | $26.41^{bcd}$ | $279.7^c$ | $19.62^c$ |

Means followed by a similar letter are not significantly different.

Figure 6:
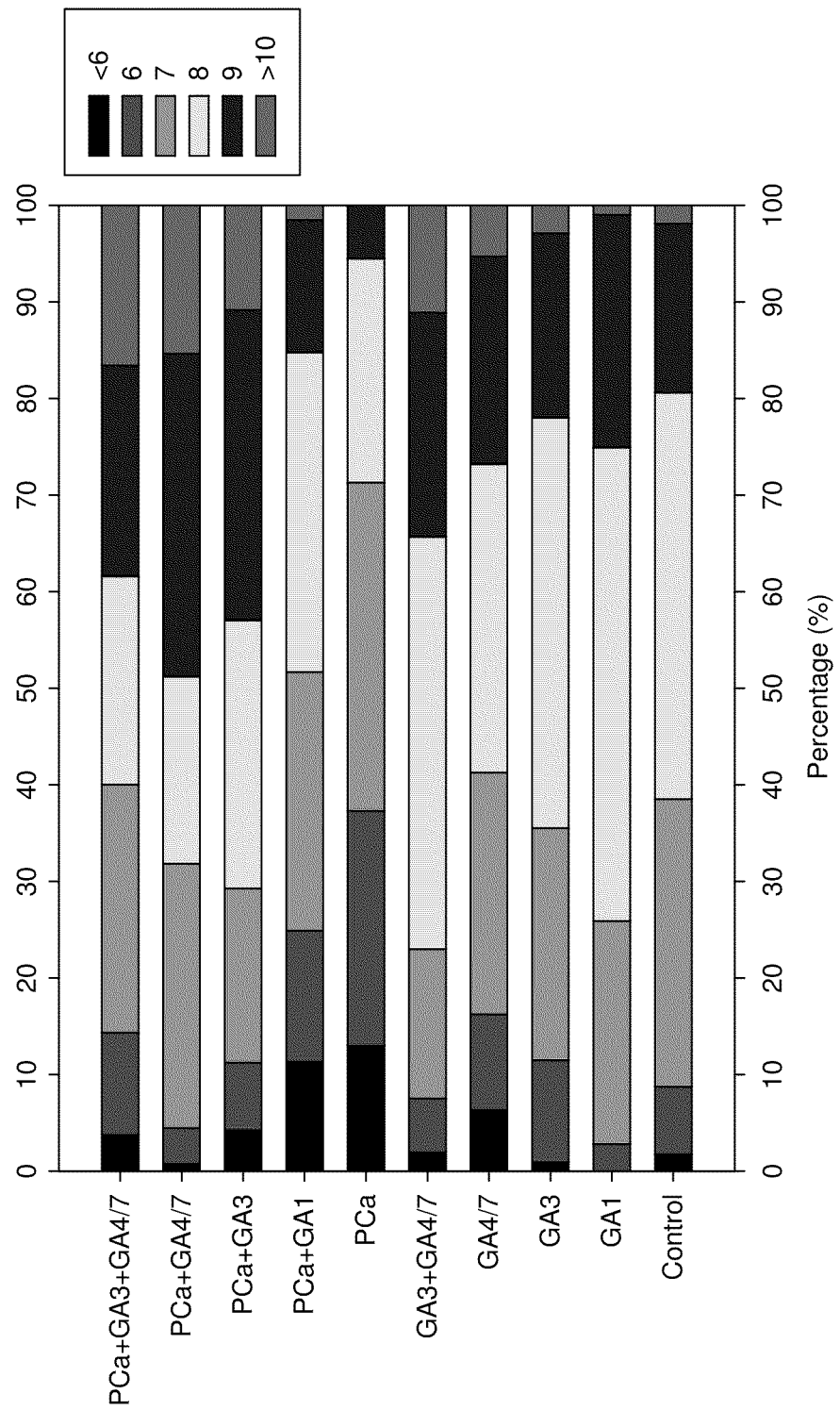
FIG. 6 is a plot showing fruit size distribution in sweet cherry cv. 'Bing' treated at 30 days after anthesis with PCa or the indicated gibberellin isomers alone or in combination. The data show distribution of every fruit from replicate limbs, and 50-300 fruit/limb were measured. Size distribution is from <6 g to >10 g, from left to right in the plot. GA1, gibberellin A1; GA3, gibberellin A3; GA4/7, mixture of gibberellin A4 and gibberellin A7. Size distribution ranges for treatments are as follows: GA1 ranges from 6 g to >10 g; PCa ranges from <6 g to 9 g; all others range from <6 g to >10 g.
Figure 7:
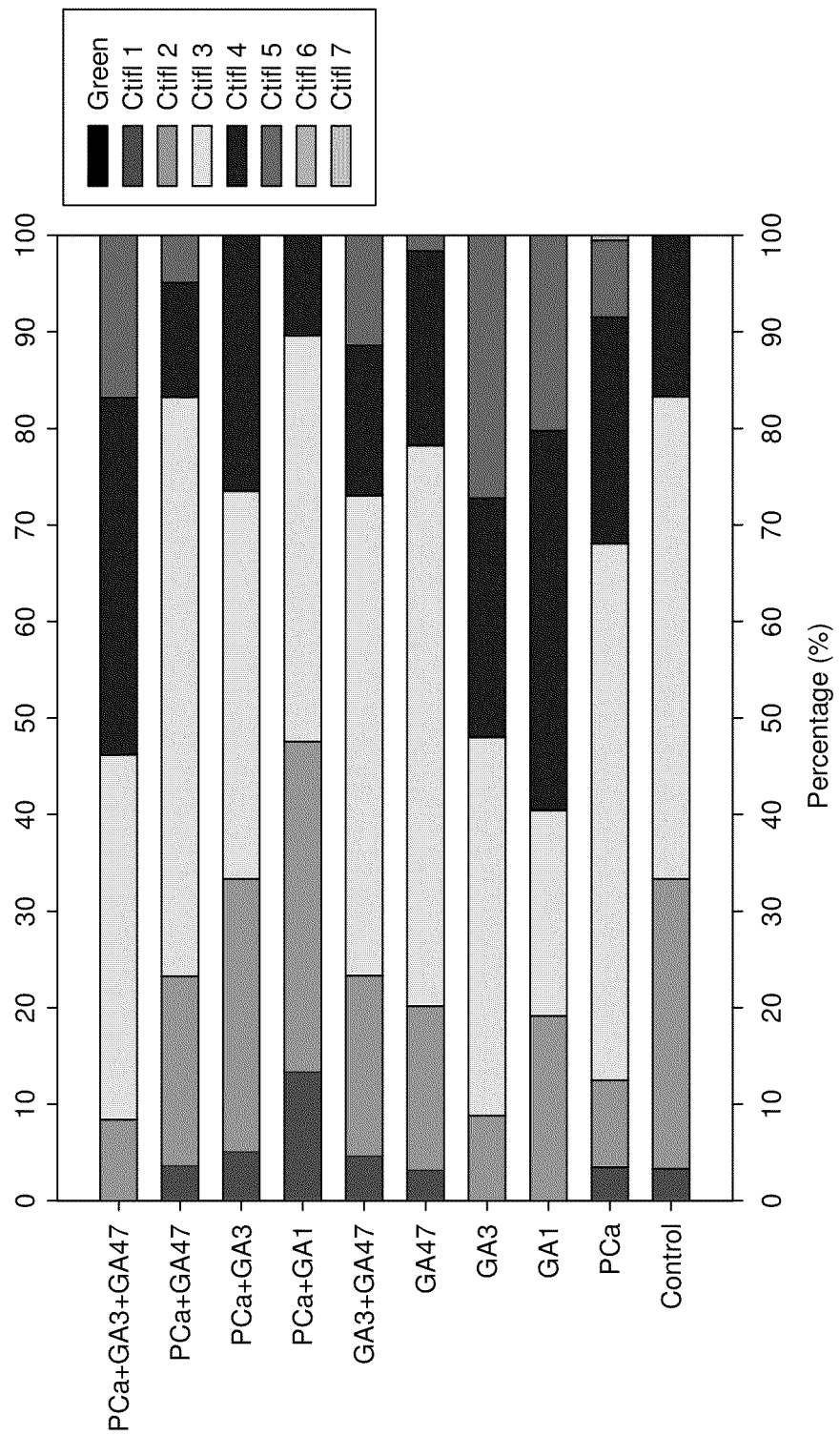
FIG. 7 is a plot showing fruit color distribution in sweet cherry cv. 'Bing' treated with PCa or gibberellin isomers alone or in combination, applied at 30 days after anthesis. Color distribution is from green to Ctifl 7, from left to right of the plot. Color distribution ranges for treatments are as follows: PCa+GA3+GA4/7, GA3, and GA1, each range from Ctifl 2 to Ctifl 5; PCa+GA4/7, GA3+GA4/7, and GA 4/7 each range from Ctifl 1 to Ctifl 5; PCa+GA3, PCa+GA1, and control each range from Ctifl 1 to Ctifl 4; PCa ranges from Ctifl 1 to Ctifl 6.

The combinations of PCa+$GA_3$ and PCa+$GA_{4/7}$ improved fruit weight by about 15%. Further, the percent of fruit ≥9 g from these PCa+GA treatments was about 45% as compared to only 20% of the same size fruit in the untreated control (FIG. 6). These combinations also improved fruit firmness from 245 g/mm in untreated control to 280 g/mm (Table 1). All treatments improved fruit firmness, though $GA_{4/7}$ was the least effective. A single application of GAs improved fruit soluble solids. This effect was tempered when GA was combined with PCa (Table 1). Fruit exocarp color development was delayed when GAs were combined with PCa (FIG. 7).

Figure 8:
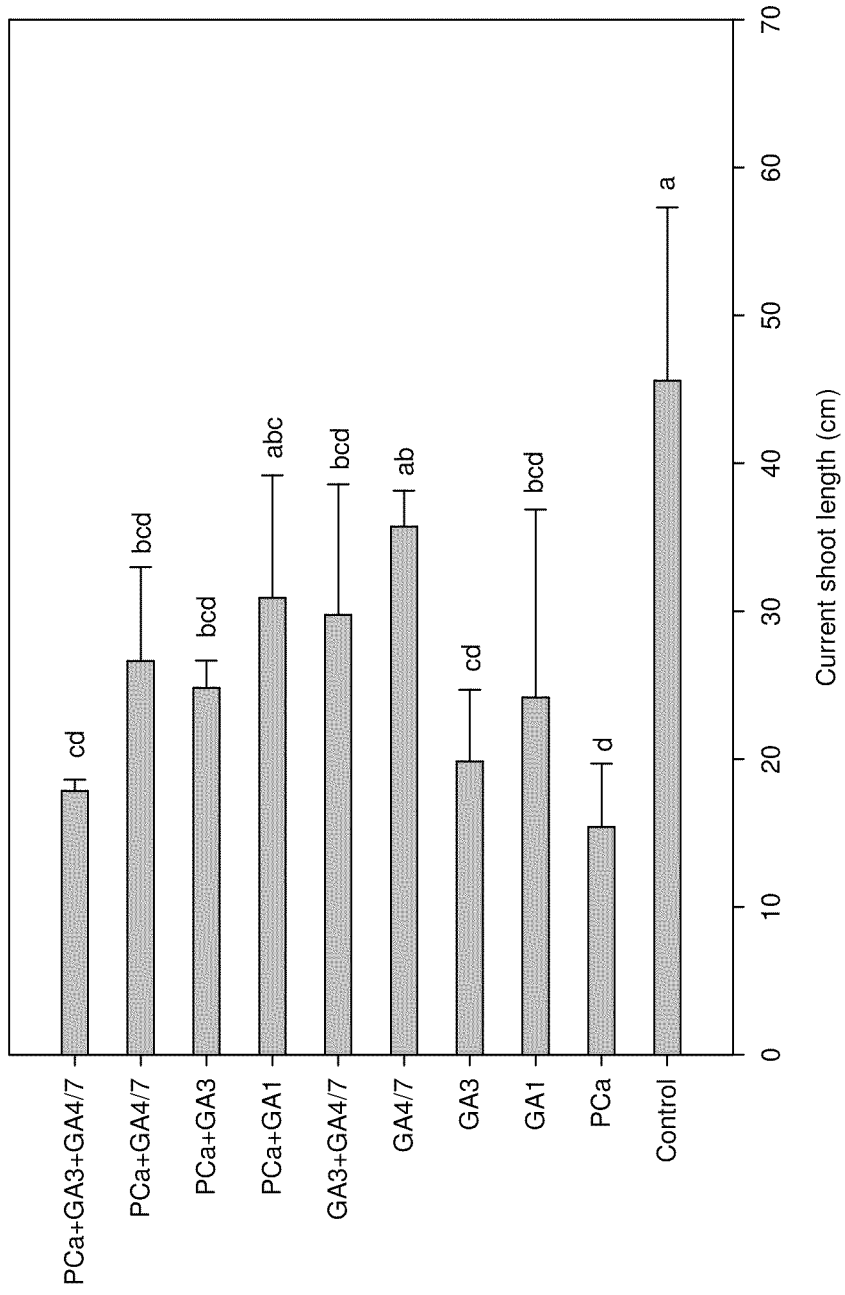
FIG. 8 is a graph showing current shoot length in sweet cherry cv. 'Bing' treated with PCa or gibberellin isomers alone or in combination, applied at 30 days after anthesis. Data were collected after shoot growth termination about three months following application. Values marked with the same letter do not differ significantly (p>0.05).

A single application of PCa effectively reduced vegetative vigor; current season extension shoots were less than half the length of untreated extension shoots after terminal bud set (FIG. 8). Investigation of flower density revealed no inhibitory effect of any treatment on return bloom.

Experiment 2

Figure 9:
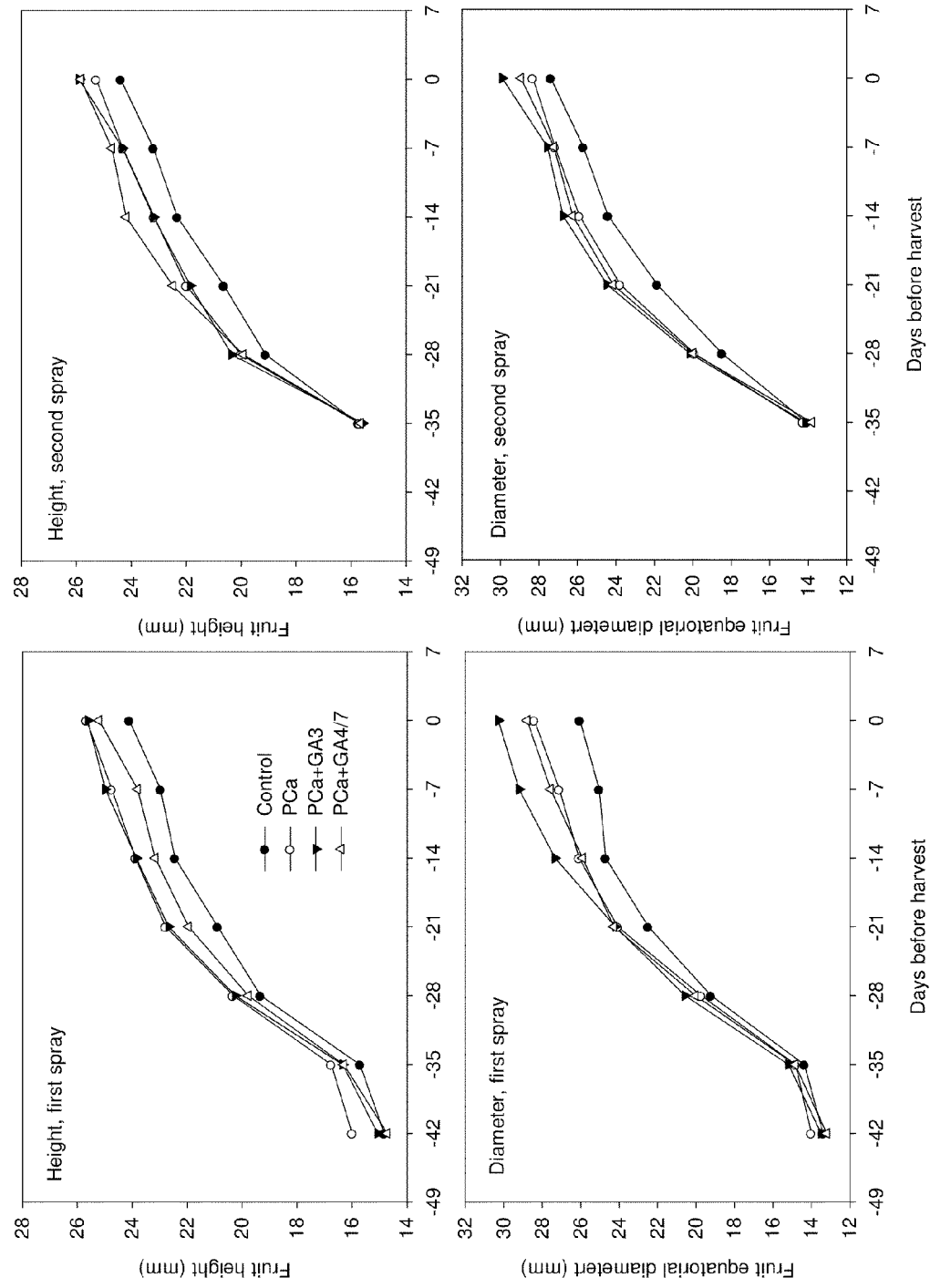
FIG. 9 is a series of graphs showing mean fruit height (upper) and mean fruit equatorial diameter (lower) in sweet cherry cv. 'Bing' treated with PCa or PCa plus gibberellin, applied at 30 days (first spray, left) or 37 days (second spray, right) after anthesis (42 or 35 days before harvest, respectively).
Figure 10:
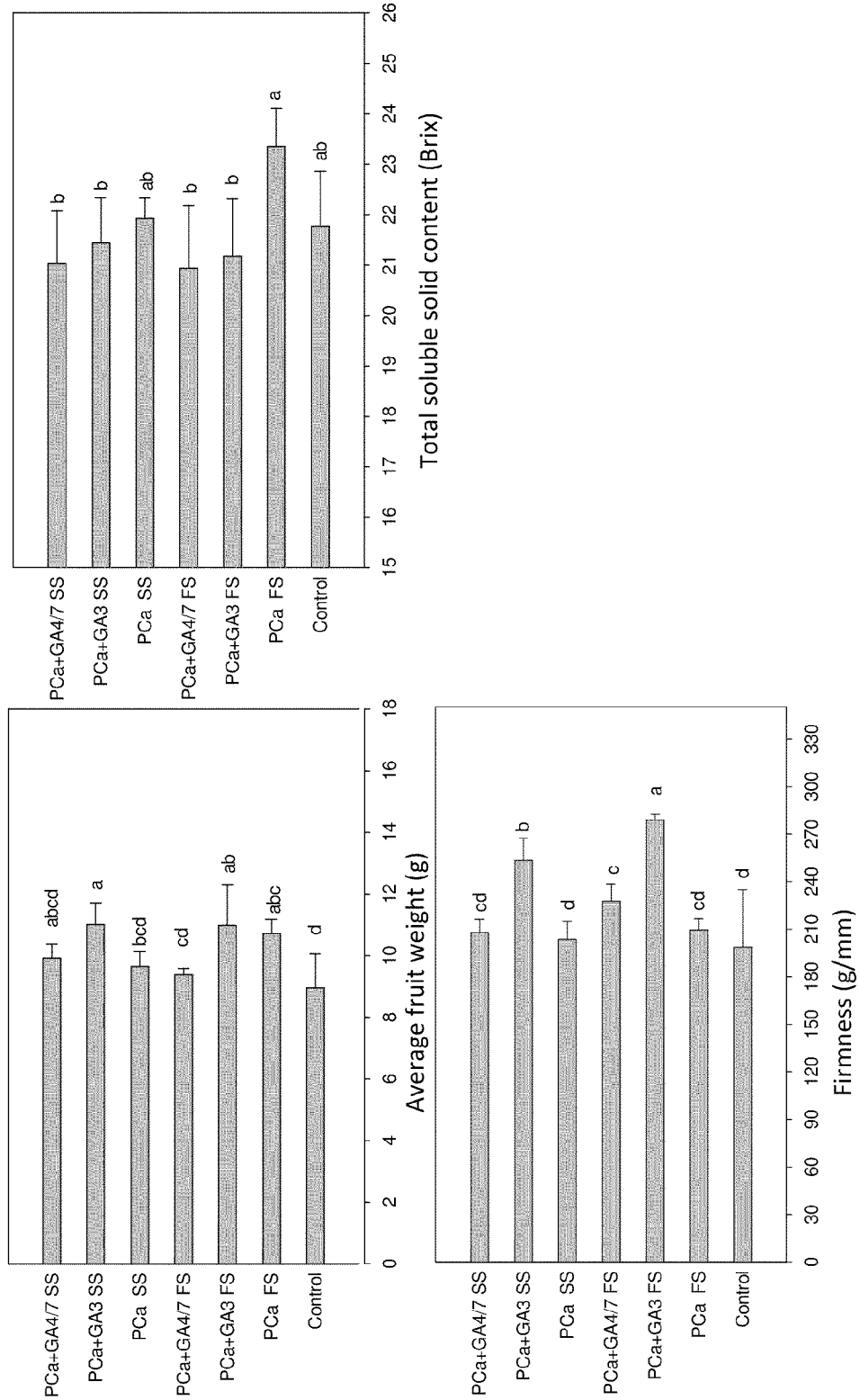
FIG. 10 is a series of graphs showing average fruit weight, total soluble solid content, and firmness of cherries at harvest from sweet cherry cv. 'Bing' treated with PCa alone or in combination with GA3 or GA4/7, applied at day 30 (first spray, FS) or day 37 (second spray, SS) after anthesis (n=3). Values marked with the same letter do not differ significantly (p>0.05).
Figure 11:
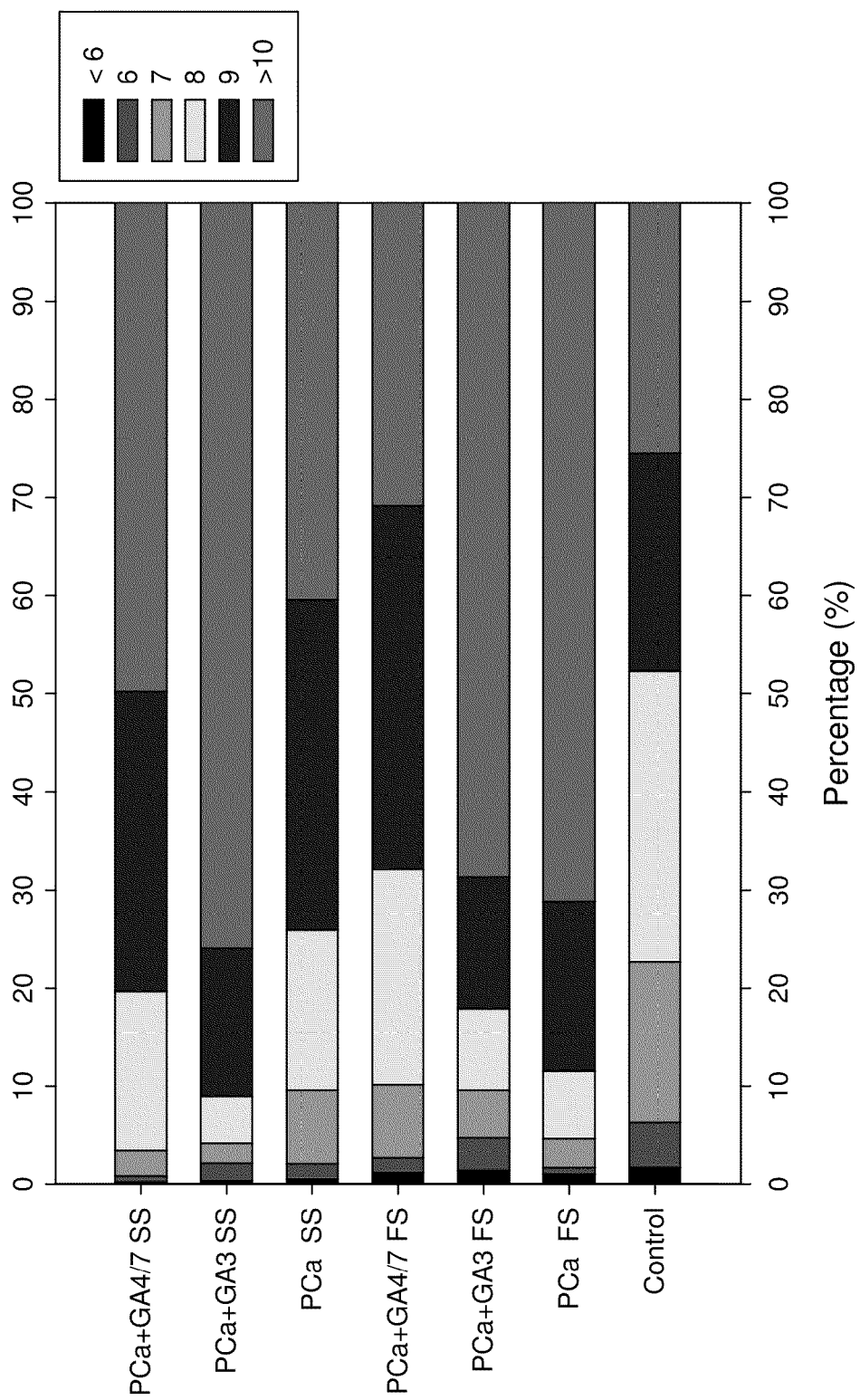
FIG. 11 is a plot showing distribution of fruit size at harvest in sweet cherry cv. 'Bing' treated with PCa alone or in combination with GA3 or GA4/7, applied at day 30 (first spray, FS) or day 37 (second spray, SS) after anthesis (n=3). Size distribution is from <6 g to >10 g, from left to right of the plot. Size distribution ranged from <6 g to >10 g for all treatments.
Figure 12:
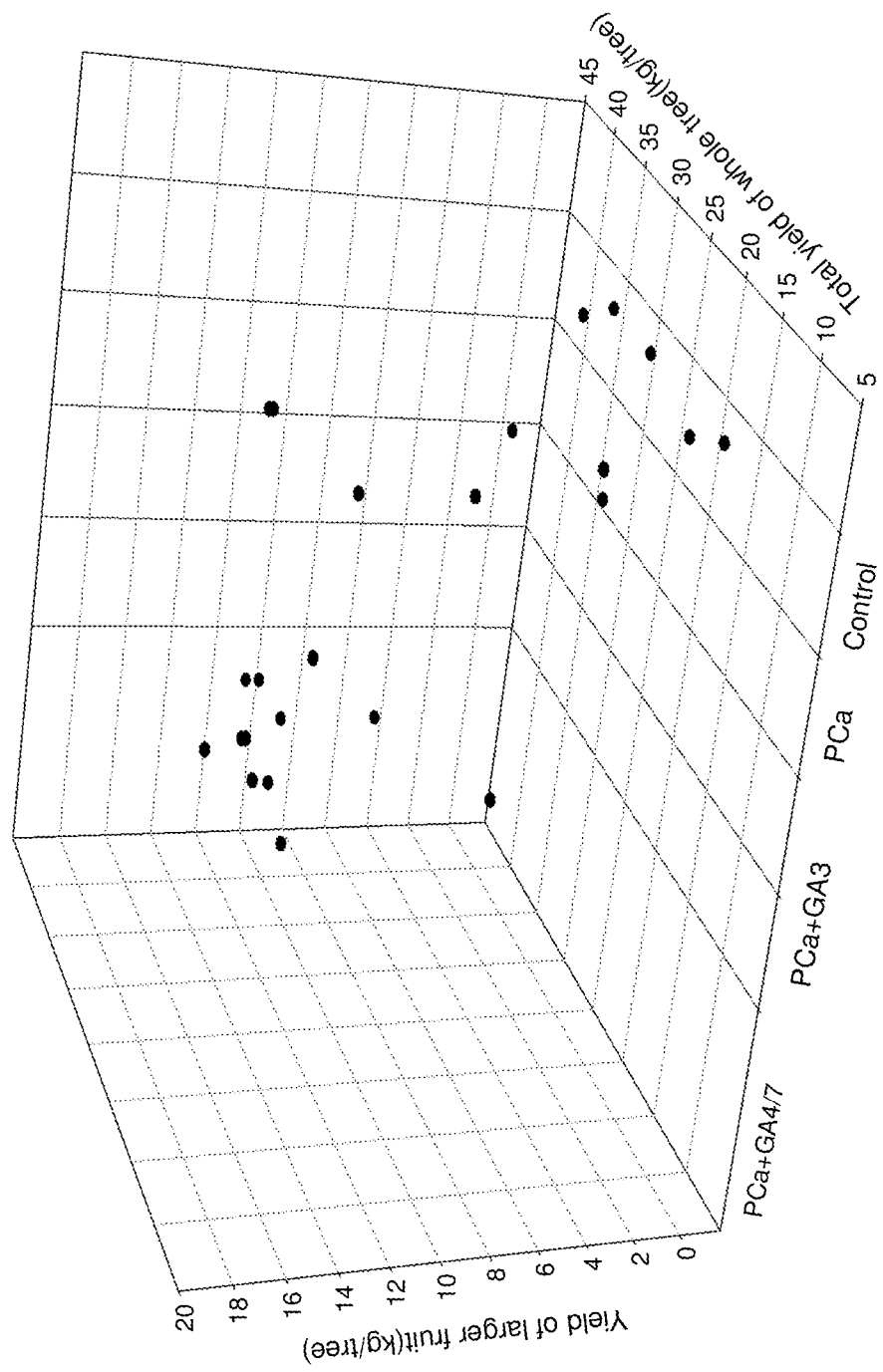
FIG. 12 is a plot showing the effect of PCa alone or in combination with gibberellins (GA3 or GA4/7) applied at early stage of fruit expansion of 'Bing' cherry (30 days after anthesis) on the relationship between yield of larger fruit (larger than 29.8 mm in diameter) and total yield on all trees.

Whole-tree applications of PCa+$GA_3$ at 30 (FS, first spray) or 37 (SS, second spray) days after anthesis significantly increased 'Bing' fruit equatorial diameter and height (FIG. 9). Further, these treatments also increased individual fruit weight by about 20% compared to untreated control (FIG. 10). In contrast, whole-tree applications of PCa+$GA_{4/7}$ did not improve fruit quality similarly. A further analysis of fruit weight distribution showed that, although both first and second spray of PCa+$GA_{4/7}$ resulted in 35-40% fruit in ≥10 g category compared with only 20% in the control, PCa+$GA_3$ had a significantly greater proportion, with 80% in this category, irrespective of application timing (FIG. 11). In addition, both first and second spray timings of PCa alone resulted in 15% increase in fruit in the ≥10 g category compared to the control. Further, a plot of crop yield/tree vs. large fruit (≥10 g) illustrated that both PCa+$GA_3$ and PCa+$GA_{4/7}$ treatments improved crop yield and fruit size in sweet cherry cv 'Bing' (FIG. 12). In addition, cherry trees treated with PCa+$GA_3$ had more marketable yield than those treated by PCa+$GA_{4/7}$ in both spray dates in this study (FIGS. 10 and 12).

Figure 13:
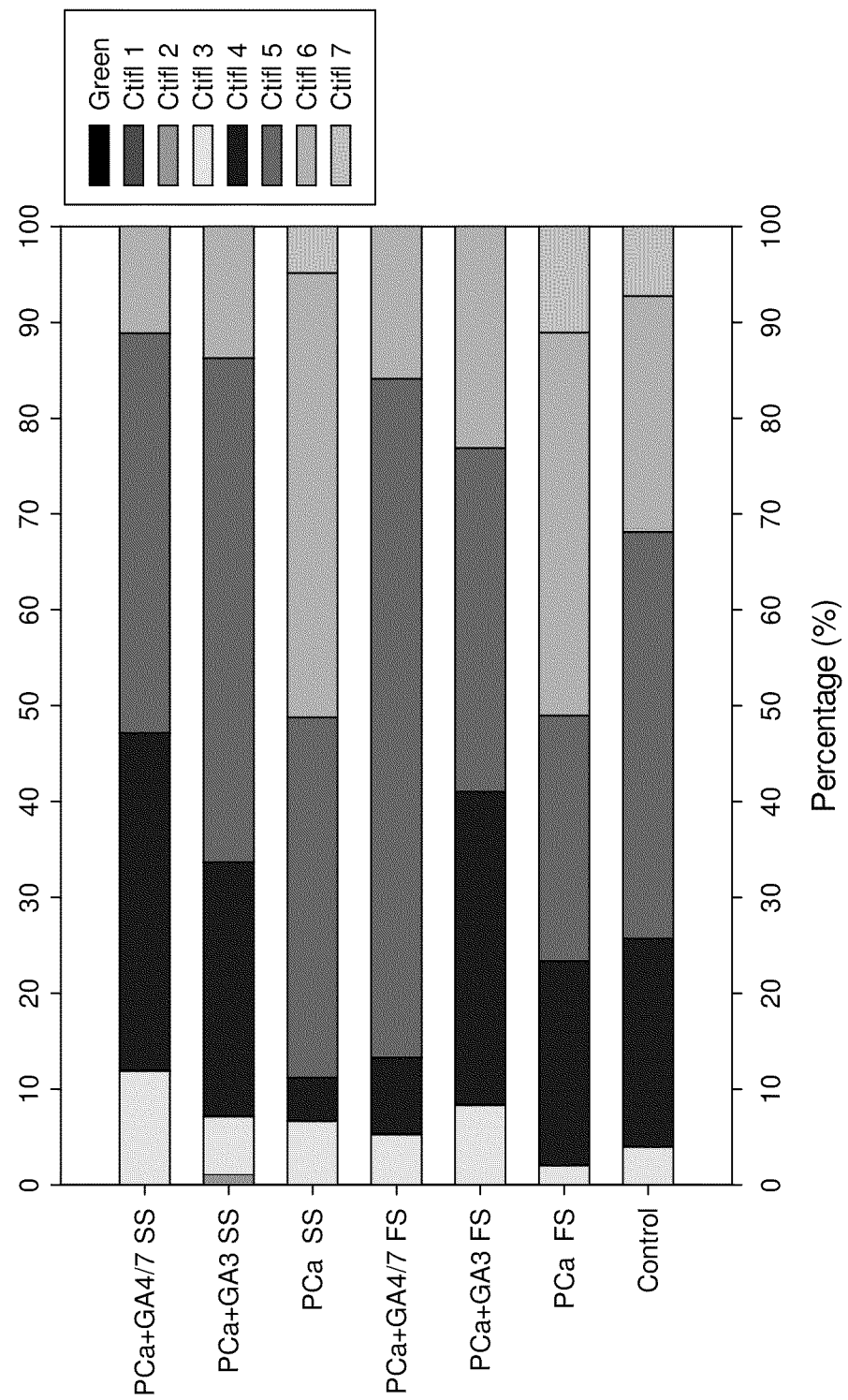
FIG. 13 is a plot showing cherry color distribution at harvest in sweet cherry cv. 'Bing' treated with PCa alone or in combination with GA3 or GA4/7, applied at day 30 (first spray, FS) or day 37 (second spray, SS) after anthesis. The graph shows percentage of cherries at each scale (green to Ctifl 7, from left to right of the plot). Size distribution ranges for treatments are as follows: PCa+GA4/7 SS, PCa SS, PCa+GA4/7 FS, and PCa+GA3 FS ranged from Ctifl 3 to Ctifl 6; PCa SS, PCa FS, and Control ranged from Ctifl 3 to Ctifl 7; and PCa+GA3 SS ranged from Ctifl 2 to Ctifl 6.

Whole tree applications of $GA_3$ or $GA_{4/7}$ plus PCa had a tendency to decrease total soluble solids levels, though this effect was not statistically significant (FIG. 10). Both single applications of PCa+$GA_3$ improved fruit firmness. Further, these treatments yielded fruit with 40% greater firmness than those of the untreated control (FIG. 10). No other treatment improved fruit firmness. Both PCa+$GA_3$ and PCa+$GA_{4/7}$ treatments delayed fruit color development and, the former induced a higher proportion of light color fruit than the latter, irrespective of timing of application (FIG. 13). Moreover, the second application timing induced greater delays of color development for both PCa plus $GA_3$ and PCa plus $GA_{4/7}$.

Figure 14:
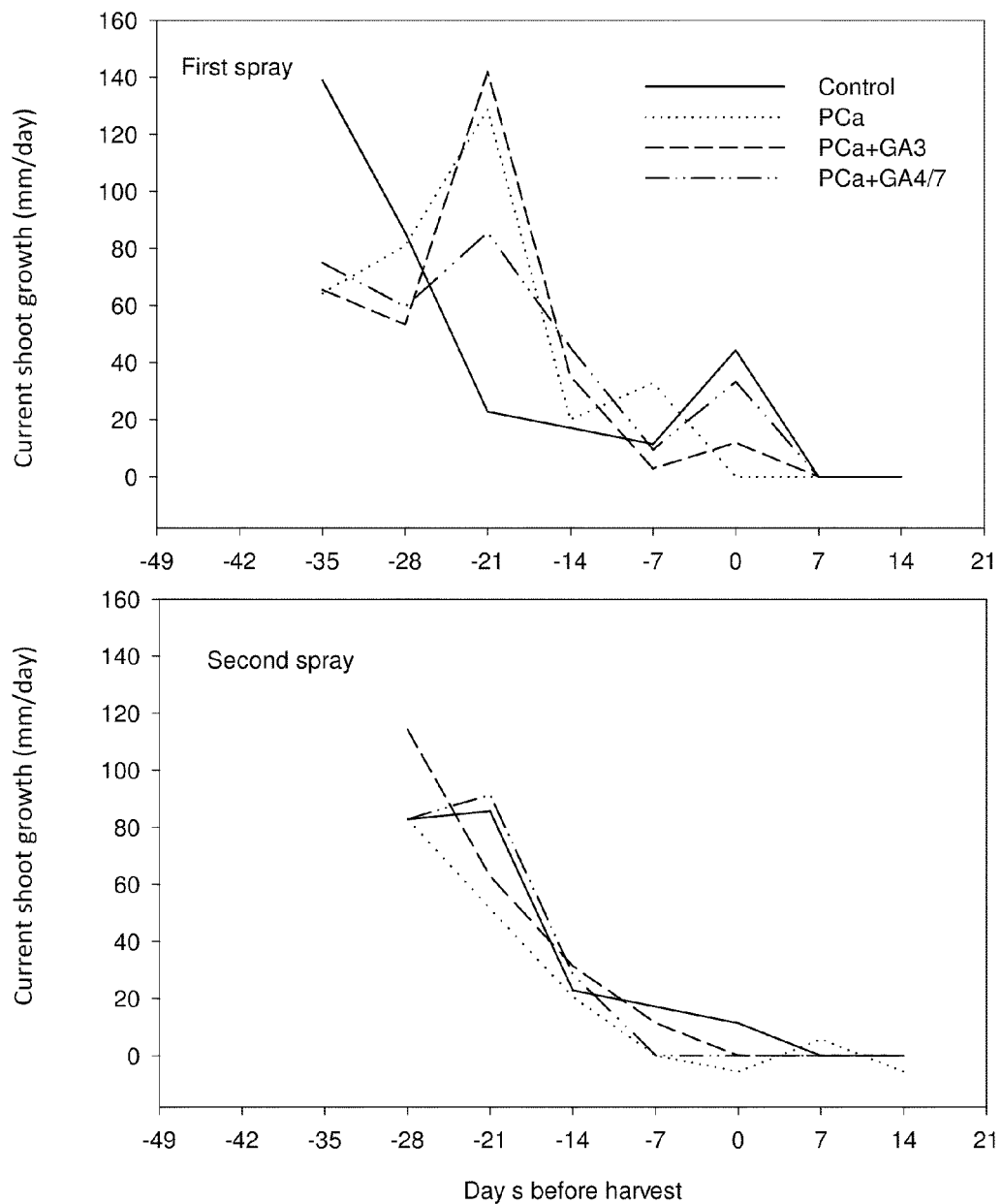
FIG. 14 is a pair of graphs showing current shoot growth in sweet cherry 'Bing' treated with PCa alone or in combination with GA3 or GA4/7, applied at day 30 (first spray, upper) or day 37 (second spray, lower) after anthesis.

Current shoot growth showed a different pattern between the two spray dates. No differences in shoot growth among treatments were recorded during the two weeks following application (FIG. 14). Three weeks after application, shoots in PCa+$GA_3$ and PCa+$GA_{4/7}$-treated trees exhibited higher rates of growth than the control and PCa treatment (FIG. 14). PCa+$GA_3$-treated trees also showed a higher shoot length than other treatments. Irrespective of timing, a single spray of PCa reduced shoot growth compared with the control and PCa+GAs.

Figure 15:
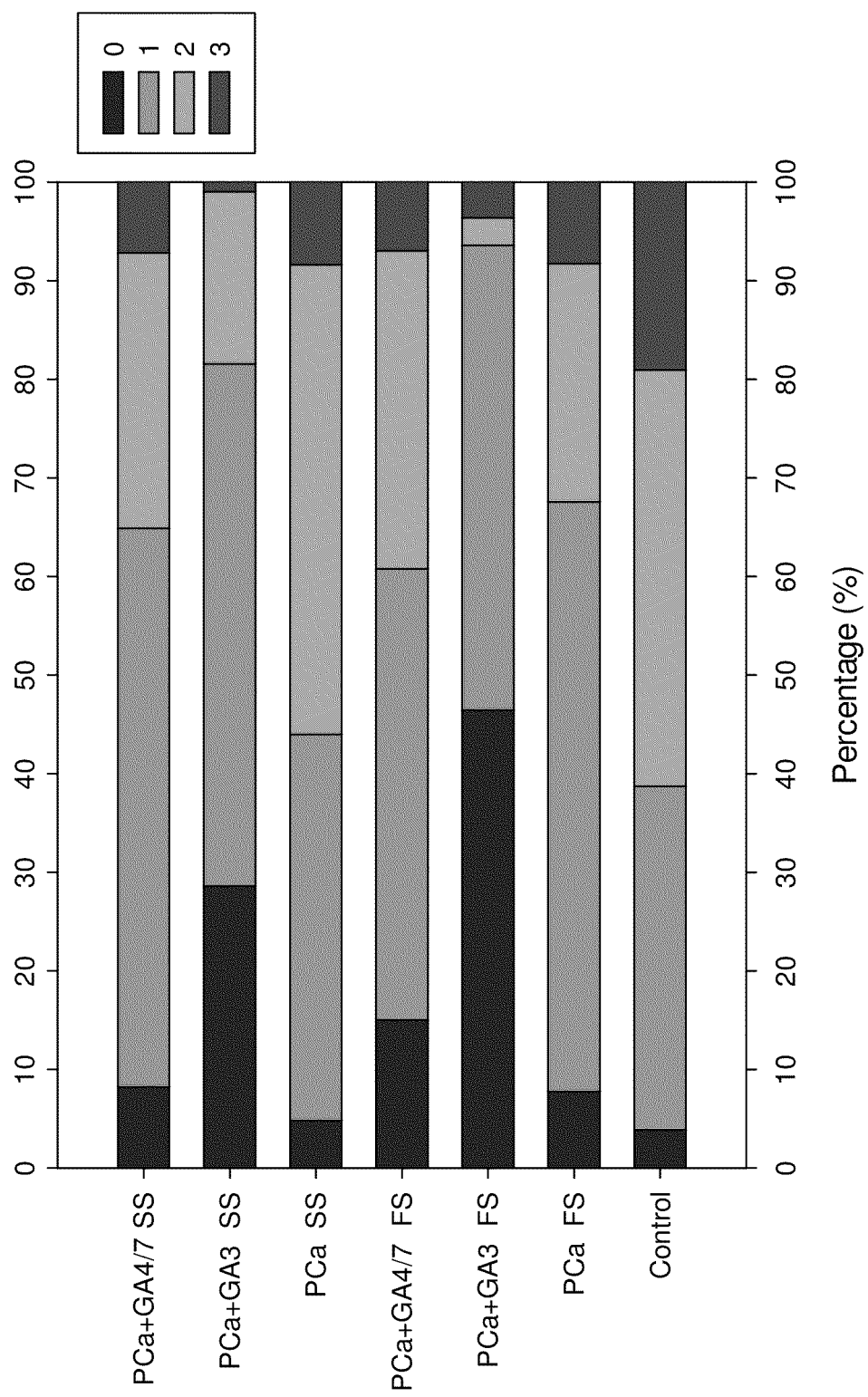
FIG. 15 is a plot showing storability of fruit from sweet cherry cv. 'Bing' treated with PCa alone or in combination with GA3 or $GA_{4/7}$, applied at day 30 (first spray, FS) or day 37 (second spray, SS) after anthesis. The plot shows the percentage of cherries at each of four categories: healthy, unblemished, and marketable (0); very slight decayed or pitted, but marketable (1); around 50% decayed or pitted and unmarketable (2); and more than 50% decayed or pitted and unmarketable (3), from left to right of the plot. Distribution ranged from 0-3 for all treatments.
Figure 16:
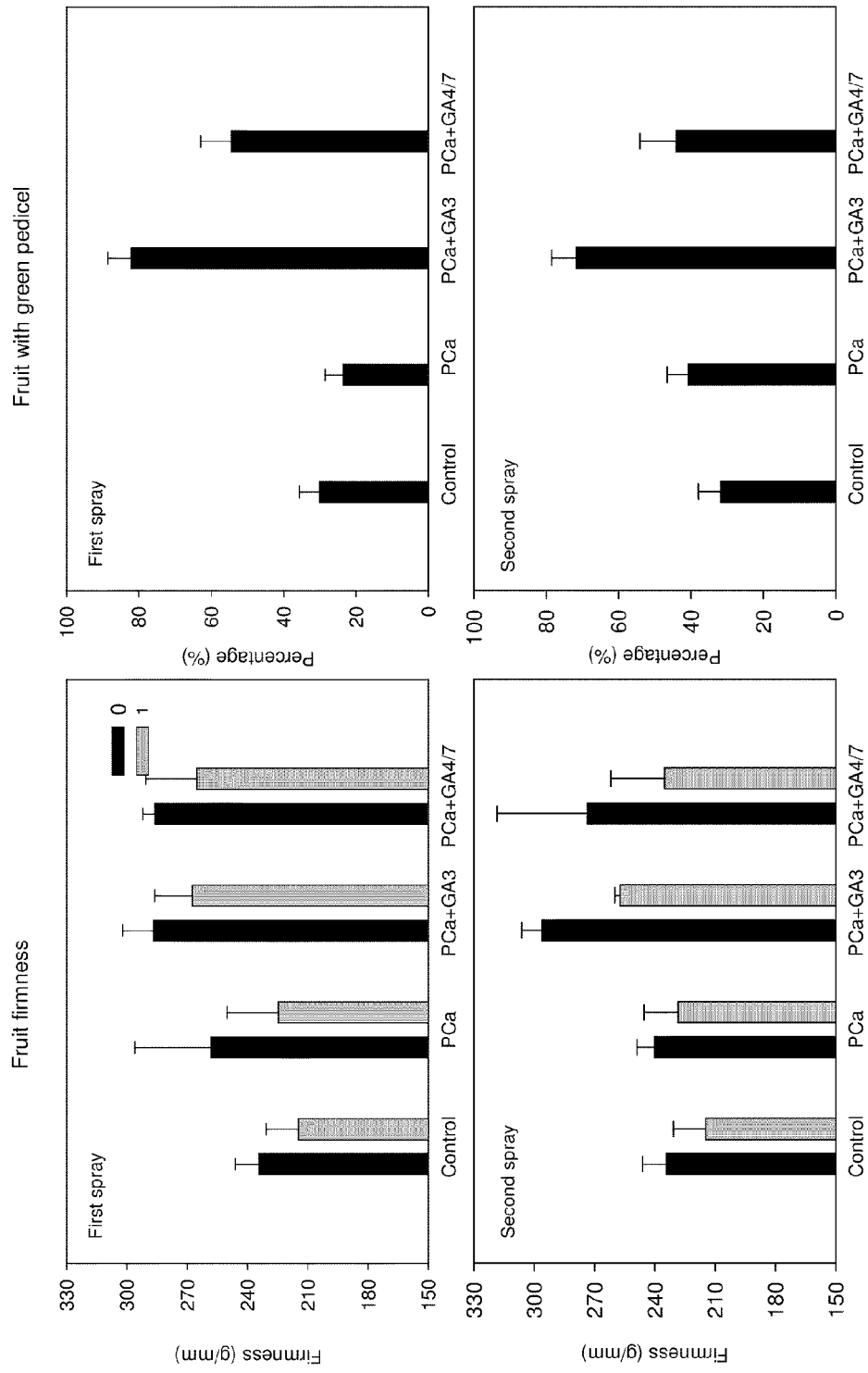
FIG. 16 is a series of graphs showing fruit firmness (left) or fruit with green pedicel (right) after 30 days of storage. Fruit were from sweet cherry cv. 'Bing' treated with PCa alone or in combination with GA3 or GA4/7, applied at day 30 (first spray, top) or day 37 (second spray, bottom) after anthesis. The graphs show percentage of cherries at two categories: healthy (0) or partly decayed or pitted (1) for fruit firmness data. Error bars indicate standard deviation of the mean.

An investigation of fruit storability showed that both pre-harvest PCa+$GA_3$ and PCa+$GA_{4/7}$ treatments improved fruit storability (FIG. 15). After 30 days in storage at 4° C., only 5% fruit from untreated trees were categorized as healthy (free from decay, pitting, visual defects) and fewer than 10% of PCa-treated fruit were in the same category. In contrast, fruit treated with PCa+$GA_3$ were 46% and 30% healthy in response to FS and SS, respectively. Further, nearly 90% of fruit treated with PCa+$GA_3$ were rated marketable (category 0 and 1). Treatment with PCa+$GA_{4/7}$ at both timings also improved fruit storability compared to untreated fruit, though not as effectively as PCa+$GA_3$. The percentage of fruit with green and turgid pedicels after storage was highest from the PCa+$GA_3$ treatment for both FS and SS (>80%). This compared with 55%, 24%, and 30% of similar quality pedicels from first spray treatments of PCa+PCa, and the control, respectively (FIG. 16). Moreover, earlier sprays of PCa+$GA_3$ or PCa+$GA_{4/7}$ before harvest had more beneficial effects on fruit storability. Further, fruit firmness evaluations showed that PCa+GA$_3$ treated cherries were significantly firmer than those in other treatments, and these can be evidenced by the difference of fruit firmness from category 0 (healthy) and 1 (partial decay and pitting) between treatments (FIG. 16).

To investigate whether the stored cherries could meet consumers' sensory preference, a study of sensory taste quality was conducted following storage. Fruit treated with PCa+GA$_3$ from both spray timings received the highest scores from all subjects according to the response of the cherry crew, including sweetness, tartness, cherry flavor, appearance, and overall acceptance. Fruit treated with PCa+GA$_3$ showed firmer, sweeter, more cherry flavor intensity than those treated by other treatments.

PCa is an inhibitor of GA biosynthesis and can control vegetative extension growth in apple and sweet cherry (Elfving et al., *Acta Hort.* 667:439-446, 2005). The competition between vegetative and reproductive sinks has been demonstrated in sweet cherry (Whiting and Lang, *J. Am. Soc. Hort. Sci.* 129:407-415, 2004). In the experiments described in this Example, reductions in vegetative extension growth were observed with PCa treatments, in particular at about 2 weeks after first spray. Without being bound by theory, it is believed that reductions in vegetative sink activity from applications of PCa favor assimilate partitioning to cherry fruit growth.

Figure 17:
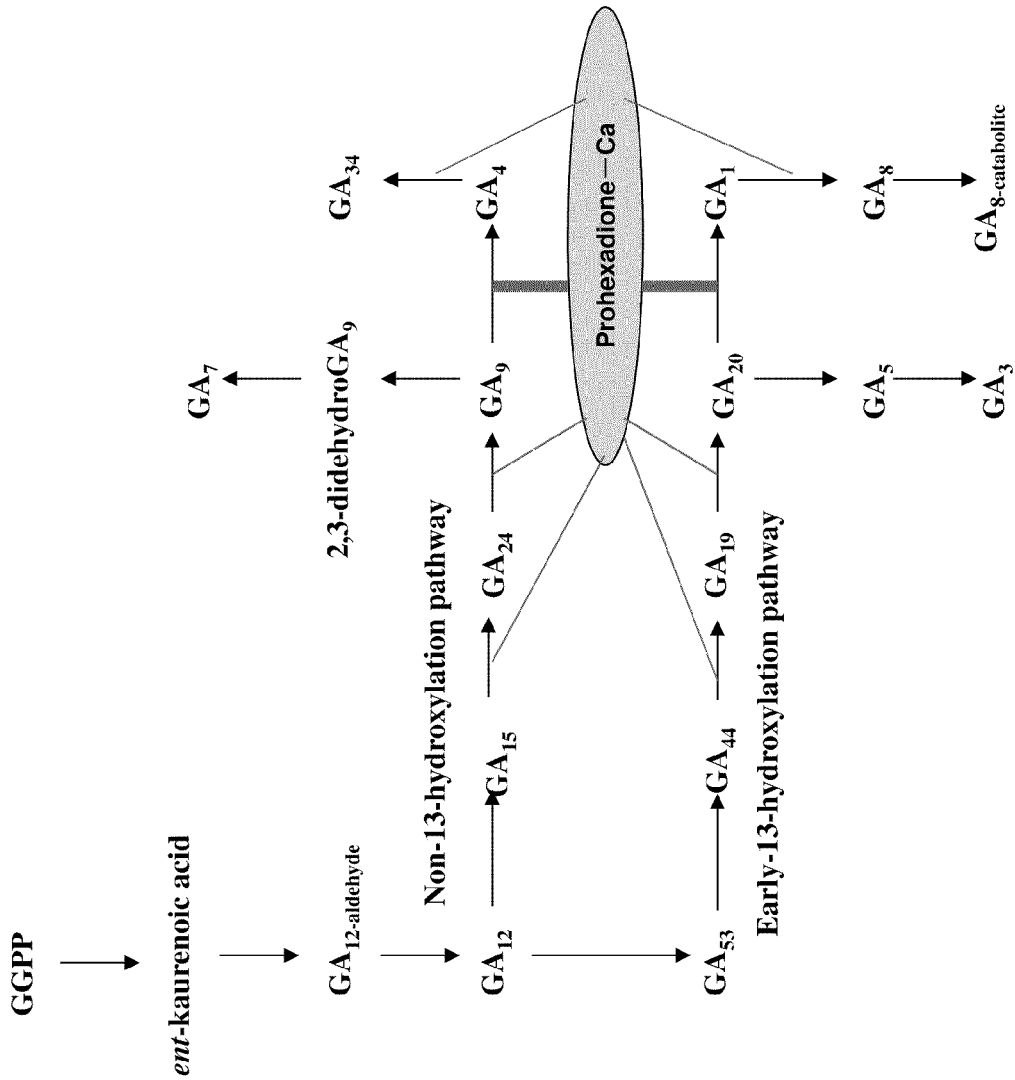
FIG. 17 is a diagram of an exemplary gibberellin biosynthetic pathway from geranylgeranyl diphosphate (GGPP) and points of inhibition by PCa. Thick lines represent major activity and thin lines represent minor activity of PCa, respectively.

Further, PCa is structurally similar to 2-oxoglutaric acid. This enables the compound to inhibit 2-oxoglutarate-dependent dioxygenases, which are involved in the formation of growth active gibberellins and in flavonoid metabolism (Rademacher, *Ann. Rev. Plant Physiol. Plant Mol. Biol.* 51:510-531, 2000). Gibberellic acid biosynthetic pathways are of considerable complexity in plants (*Plant Hormones: Biosynthesis, Signal Transduction, Action*! Davies (ed.), Kluwer Academic Publishers, 2004). They are divided into an early nonhydroxylation pathway, in which GA$_4$ is produced, and an early 13-hydroxylation pathway, in which GA$_1$ and GA$_3$ are produced (FIG. 17). The points of inhibition in the gibberellin-biosynthetic pathway by PCa include the 3β-hydroxylation pathway, thereby inhibiting the formation of highly active GA$_1$ and GA$_4$ from inactive precursors (Rademacher, *Ann. Rev. Plant Physiol. Plant Mol. Biol.* 51:510-531, 2000; Hedden and Kamiya, *Ann. Rev. Plant Physiol. Plant Mol. Biol.* 48:431-460, 1997). In some reports, PCa, paradoxically, leads to increases in shoot growth, most likely by protecting endogenous active GAs from being metabolically inactivated (Hisamatsu et al., *J. Jpn. Soc. Hort. Sci.* 67:537-543, 1998). The inactivation of exogenously applied GA$_3$ and GA$_4$ by 2β-hydroxylation can be inhibited by simultaneous treatment with PCa, resulting in increased GA-like activity (Nakayama et al., *Plant Cell Physiol.* 31:195-200, 1990; Nes and Venkatramesh, *Crit. Rev. Biochem. Mol. Biol.* 32:81-93, 1999). Without being bound by theory, it is believed that applications of PCa plus GA$_3$ or GA$_{4/7}$ increase the concentration of GA$_{4/7}$ and GA$_3$ in fruit mesocarp tissue, which promotes cell enlargement, a critical component of final fruit size in sweet cherry (Olmstead et al., *J. Am. Soc. Hort. Sci.* 132:697-703, 2007).

Example 3

Increasing Fruit Set and Fruit Size in Tree Fruit

This example describes increasing fruit set and fruit size in tree fruit utilizing 4-chlorophenoxyacetic acid.

Figure 18:
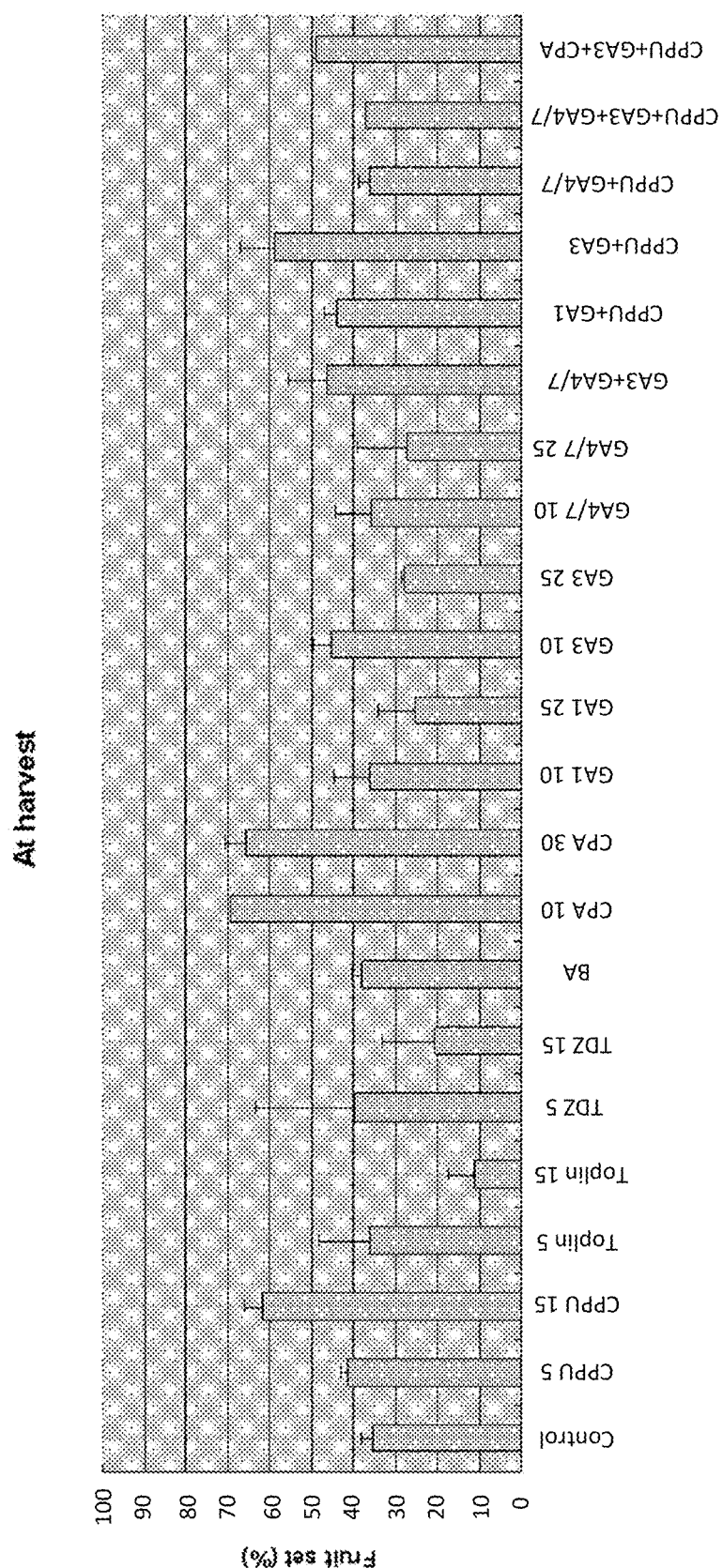
FIG. 18 is a graph showing fruit set (% of available flowers) after treatment of 'Bing' sweet cherry at full bloom with the indicated compounds. The number following each compound name indicates the parts per million (ppm) applied. CPPU, N-2-chloro-4-pyridyl)-N'-phenylurea; Toplin, 6-(3-hydroxybenzylamino) purine; TDZ, N-phenyl-N'-(1,2,3-thiadiazol-5-yl) urea; BA, N-6-benzyladenine; GA1, gibberellin A1; GA3, gibberellin A3; GA4/7, mixture of gibberellin A4 and gibberellin A7; CPA, 4-chlorophenoxyacetic acid.

Plant growth regulators were applied to limbs of sweet cherry cv. 'Bing' at full bloom when essentially all flowers were open. Fruit set was recorded as a percent of available flowers from flower counts made prior to application and fruit counts made just prior to harvest. Fruit set in trees treated with 4-chlorophenoxyacetic acid (CPA) at 10 or 30 ppm was higher than untreated control in both small and large scale trials (FIG. 18). Fruit set and fruit size at harvest were also increased in cultivars 'Bing,' 'Tieton,' and '8011-3' treated with 30 ppm CPA applied to the flowers at full bloom. (Table 2).

TABLE 2

Fruit set and fruit size at harvest

| | Fruit Set (%) | | Average fruit size (g) | |
| --- | --- | --- | --- | --- |
| Cultivar | 4-CPA | Untreated | 4-CPA | Untreated |
| Bing | 58.0 | 30.0 | 8.4 | 7.3 |
| Tieton | 35.0 | 26.0 | 8.6 | 7.2 |
| 8011-3 | 16.0 | 7.0 | 13.6 | 10.5 |

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of decreasing cold damage to a fruit tree, comprising applying to the fruit tree an effective amount of a composition comprising DL-β-aminobutyric acid (BABA) about 7 to 10 days prior to full bloom, thereby decreasing cold damage to the fruit tree.

2. The method of claim 1, wherein the composition is applied to the fruit tree leaves, buds, flowers, branches, or a combination of two or more thereof.

3. The method of claim 1, wherein the composition comprising BABA comprises about 100-200 ppm of BABA.

4. The method of claim 1, wherein the fruit tree comprises a stone fruit tree or a pome fruit tree.

5. The method of claim 4, wherein the stone fruit tree is selected from the group consisting of sweet cherry, tart cherry, plum, peach, nectarine, and apricot.

6. The method of claim 4, wherein the pome fruit tree is selected from the group consisting of apple, pear, quince, and loquat.

7. The method of claim 1, wherein decreasing cold damage comprises decreasing flower kill, increasing leaf area, increasing leaf chlorophyll content index, increasing pistil survival, increasing fruit set, increasing fruit size, or a combination of two or more thereof following exposure to temperatures of about 0° C. or less.

* * * * *